United States Patent
Karin et al.

(12) 
(10) Patent No.: US 6,316,420 B1
(45) Date of Patent: Nov. 13, 2001

(54) DNA CYTOKINE VACCINES AND USE OF SAME FOR PROTECTIVE IMMUNITY AGAINST MULTIPLE SCLEROSIS

(75) Inventors: Nathan Karin, Haifa; Sawsan Youssef, Rama Villag; Gizi Wildbaum, Kiriat-Yam, all of (IL)

(73) Assignee: Technion Research and Development Foundation LTD., Haifa (IL)

( * ) Notice: Subject to any disclaimer, the term of this patent is extended or adjusted under 35 U.S.C. 154(b) by 0 days.

(21) Appl. No.: 09/123,485

(22) Filed: Jul. 28, 1998

(51) Int. Cl.[7] .................. A61K 48/00; A61K 35/00; C12N 15/63; C12N 15/85

(52) U.S. Cl. ................ 514/44; 435/370.1; 435/325; 424/93.21; 424/932

(58) Field of Search ................ 435/320.1, 325; 514/44; 424/93.2, 93.21

(56) References Cited

FOREIGN PATENT DOCUMENTS

97/02837    2/1997    (WO).

OTHER PUBLICATIONS

Kaufman et al. (1995) Annu. Rev. Immunol., vol. 13, 339–367, 1995.*
Verma et al. (1997) Nature, vol. 389, 239–242.*
Marshall et al. (1995) Science, vol. 269, 1050–1055.*
Orkin et al. (1995) "Report and Recommendations of the Panel . . . ".*
Braciak et al. (1994) FASEB, vol. 8 (4), A201.*
Cao et al. (1997) Gastroenterology, vol. 112 (2), 501–510.*
Cash et al. (1994) J. Immunol., vol. 153, 4258–4267.*

* cited by examiner

*Primary Examiner*—Scott D. Priebe
*Assistant Examiner*—Anne Marie S. Beckerleg

(57) ABSTRACT

A method for treating a mammal for inducing protective immunity against an autoimmune disease including the step of administering to the mammal a therapeutic composition including a recombinant construct including an isolated nucleic acid sequence encoding a cytokine, the nucleic acid sequence being operatively linked to one or more transcription control sequences. A method for treating a mammal for inducing protective immunity against an autoimmune disease including the steps of (a) removing cells of the mammal; (b) transducing the cells in vitro with a recombinant construct including an isolated nucleic acid sequence encoding a cytokine, the nucleic acid sequence being operatively linked to one or more transcription control sequences; and (c) reintroducing the transduced cells to the mammal. A pharmaceutical composition including (a) a recombinant construct including an isolated nucleic acid sequence encoding a cytokine, the nucleic acid sequence being operatively linked to one or more transcription control sequences; and (b) a pharmaceutically acceptable carrier. And an antibody raised against a cytokine expressed by cells transduced with a recombinant construct including an isolated nucleic acid sequence encoding the cytokine, the nucleic acid sequence being operatively linked to one or more transcription control sequences.

4 Claims, 12 Drawing Sheets

(2 of 12 Drawing Sheet(s) Filed in Color)

No EAE pcDNA3 alone

DNA CYTOKINE VACCINES AND USE OF SAME FOR PROTECTIVE IMMUNITY AGAINST MULTIPLE SCLEROSIS

FIELD AND BACKGROUND OF THE INVENTION

The present invention relates to DNA vaccines and DNA vaccination, and more particularly, to DNA encoding cytokines and the use of same as DNA vaccines for inducing protective immunity against autoimmune diseases. Most particularly, the present invention relates to DNA encoding C-C chemokines and tumor necrosis factor alpha and the use of same for protective immunity against multiple sclerosis.

Experimental autoimmune encephalomyelitis (EAE) is an autoimmune disease of the central nervous system (CNS) which, for many years and for a variety of experimental protocols, serves as a model for the human disease, multiple sclerosis (MS), a chronic degenerative disease marked by patchy destruction of the myelin that surrounds and insulates nerve fibers and mild to severe neural and muscular impairments, since in both diseases circulating leukocytes penetrate the blood brain barrier and damage myelin resulting in impaired nerve conduction and paralysis (1, 2).

Molecular biologic techniques were previously used to follow leukocyte trafficking to the site of inflammation at the CNS of EAE rats, and a model that characterizes this process as a sequential multi-step event was suggested (3).

At first, a very limited repertoire of T-cells, named "the primary influx" interact with their target antigen at the site of inflammation, leading to the activation of the blood brain barrier to express various adhesion molecules and thus to increase its permeability to circulating leukocytes (3, 4). Enhanced permeability of this barrier allows a non-selective influx of leukocytes, which are named "the secondary influx". This influx correlates with disease onset (3, 5). Subsequently, antigen specific autoimmune T-cells either become anergic or undergo programmed cell death (apoptosis) leading to a remission in disease severity (6). Inhibition of the secondary influx, by either soluble peptide therapy or anti-adhesion molecule blockade effectively prevented, or even reversed, an ongoing disease even though the primary influx remained apparent at the site of inflammation (3–5, 7). Taken together these results not only suggest novel therapeutic strategies, but also emphasize the important role of the non-selective leukocyte influx to a site of inflammation.

Chemokines are chemoattractants that mediate leukocyte attraction and recruitment at the site of inflammation. As such, they are likely to be key mediators in the recruitment of the secondary influx of leukocytes at an inflamed target organ. This has motivated us to use the novel technology of naked DNA vaccination (8–17) and explore the therapeutic potential of anti-chemokine immunotherapy in EAE.

Based on the positions of the first two cysteines, the chemokines can be divided into four highly conserved but distinct supergene families C-C, C-X-C, C and the newly discovered C-X3-C (18, 19). The C-C family is primarily involved in the activation of endothelium and for chemoattraction of T cells and monocytes to the site of inflammation (20–32). The protective competence of anti-C-C chemokine based immunotherapy has been demonstrated by Karpus at al. who blocked EAE in mice by immunizing them with rabbit anti-mouse polyclonal antibodies against macrophage inflammatory protein-1 α (MIP-1α) (33), and very recently by Gong at al. who used an antagonist of monocyte chemoattractant protein 1 is (MCP-1) to inhibit arthritis in the MRL-1pr mouse model (34). In another study Berman at al. used in situ hybridization to demonstrate the dominant expression of MCP-1 in rat EAE brain (35).

In the course of reducing the present invention down to practice we have cloned each of the major C-C chemokines: MCP-1, MIP-1α, macrophage inflammatory protein-1β (MIP-1β) and regulation on activation normal T expressed and secreted (RANTES) from EAE brains into an eukaryotic expression vector and determined their capacity to block EAE when used as vaccines.

Thus, during the course of EAE various proinflammatory cytokines and chemokines are produced at the site of inflammation (40, 53–55). The pivotal role of one of these proinflammatory cytokines; tumor necrosis factor alpha (TNF-α), in EAE has been well characterized. TNF-α is produced by activated T cells (mostly Th1) and macrophages, and its elevated expression at the site of inflammation occurs during the critical phase of disease (55), at the time when the 'secondary influx' of leukocytes is apparent (3). Except for a single recent study carried out in genetically modified animals (56), all investigators agree that TNF-α contributes to the proinflammatory process in EAE and MS (57–71). Early studies have shown that IFN-γ and TNFα together exhibit a synergistic effect on enhancing expression of adhesion molecules on endothelial cells (61), and on eliciting the inflammatory process, which can be reversed by either anti-adhesion molecule immunotherapy (4), or by blocking TNF-α (57–61). More recent studies have demonstrated that inhibition of TNF-α activity by either neutralizing antibodies, or soluble TNF receptor therapy, effectively prevent, or even reverse EAE (62, 64, 66–71). Overexpression of TNF-α at the CNS aggravated the disease (65), whereas genetically impaired expression of this gene inhibited disease development and progression (63).

A major disadvantage in treating chronic diseases with xenogenic neutralizing antibodies lies in their immunogenicity. This has motivated investigators to develop chimeric humanized antibodies (reviewed in 50), and monoclonal antibodies engineered with human Ig heavy and light chain yeast artificial chromosome (YAC) (51). However, following repeated immunization, these engineered antibodies do trigger an apparently allotypic response.

The therapeutic strategy of the present invention, is of advantage over the above methods since it resulted in the generation of immunity to autologous antigens.

There is thus a widely recognized need for, and it would be highly advantageous to have, methods and compositions enabling vaccination with DNA encoding cytokines, such as C-C chemokines and tumor necrosis factor alpha and the use of such vaccination for protective immunity against multiple sclerosis, devoid of the limitations associated with the use of neutralizing antibodies.

SUMMARY OF THE INVENTION

DNA vaccination represents a novel means of expressing antigen in vivo for the generation of both humoral and cellular immune responses. The present invention uses this technology to elicit protective immunity against autoimmune diseases as exemplified by the experimental autoimmune encephalomyelitis (EAE), a T cell mediated autoimmune disease of the central nervous system that serves as an experimental model for multiple sclerosis.

RT-PCR verified by Southern blotting and sequencing of PCR products of four different C-C chemokines: MIP-1α, MCP-1, MIP-1β and RANTES was performed on brain samples from EAE rats to evaluate mRNA transcription at different stages of disease. Each PCR product was then used as a construct for naked DNA vaccination. The subsequent in vivo immune response to MIP-1α or MCP-1 DNA vaccines prevented EAE, even if disease was induced two months after administration of naked DNA vaccines. In contrast, administration of the MIP-1β naked DNA significantly aggravated the disease. Generation of in vivo immune response to RANTES naked DNA had no notable effect on EAE. MIP-1α, MCP-1 and MIP-1β mRNA transcription in EAE brains peaked at the onset of disease and declined during its remission, whereas RANTES transcription increased in EAE brains only following recovery. Immunization of CFA without the encephalitogenic epitope did not elicit the anti C-C chemokine regulatory response in DNA vaccinated rats. Thus, modulation of EAE with C-C chemokine DNA vaccines is dependent targeting chemokines that are highly transcribed at the site of inflammation at the onset of disease.

We further demonstrate herein that EAE rats display a significantly increased TNF-α specific antibody titer as compared to rats immunized in hind foot pads with Complete Freund's Adjuvant (CFA) alone. A positive correlation in time course between the elevated expression TNF-α at the CNS and the production of anti-self antibodies to this proinflammatory cytokine was observed. This natural immunity to TNF-α could not block the development of disease. An administration of TNF-α naked DNA vaccine, even two months before active induction of disease, enhanced the development of in vivo immune response to self TNF-α and conferred EAE resistance. Immunization of CFA without the encephalitogenic epitope, even though induced a local inflammatory process, did not elicit the anti TNF-α regulatory response in DNA vaccinated rats. These anti-self antibodies were found capable of inhibiting the development of disease when transferred to other EAE rats. Thus, modulation of EAE with TNF-α vaccines is dependent targeting cytokine that are highly transcribed at the site of inflammation during the course of disease and therefore provides a tool by which the immune system is encouraged to elicit anti-self protective immunity to restrain its own harmful reactivity only when such a response is needed.

According to the present invention there is thus provided a method for treating a mammal for inducing protective immunity against an autoimmune disease, the method comprising the step of administering to the mammal a therapeutic composition including a recombinant construct including an isolated nucleic acid sequence encoding a cytokine, the nucleic acid sequence being operatively linked to one or more transcription control sequences.

According to the present invention there is further provided a method for treating a mammal for inducing protective immunity against an autoimmune disease, the method comprising the steps of (a) removing cells of the mammal; (b) transducing the cells in vitro with a recombinant construct including an isolated nucleic acid sequence encoding a cytokine, the nucleic acid sequence being operatively linked to one or more transcription control sequences; and (c) reintroducing the transduced cells to the mammal.

According to still further features in the described preferred embodiments the transduced cells are reintroduced to the mammal parenterally.

According to the present invention there is further provided a pharmaceutical composition comprising (a) a recombinant construct including an isolated nucleic acid sequence encoding a cytokine, the nucleic acid sequence being operatively linked to one or more transcription control sequences; and (b) a pharmaceutically acceptable carrier.

According to further features in preferred embodiments of the invention described below, the pharmaceutically acceptable carrier is selected from the group consisting of an aqueous physiologically balanced solution, an artificial lipid-containing substrate, a natural lipid-containing substrate, an oil, an ester, a glycol, a virus and metal particles.

According to still further features ill the described preferred embodiments the composition is useful for treating an autoimmune disease.

According to still further features in the described preferred embodiments the composition is suitable for parenteral administration to a human.

According to still further features in the described preferred embodiments the pharmaceutically acceptable carrier comprises a delivery vehicle that delivers the nucleic acid sequences to the mammal.

According to still further features in the described preferred embodiments the delivery vehicle is selected from the group consisting of liposomes, micelles, and cells.

According to the present invention there is further provided an antibody raised against a cytokine expressed by cell s transduced with a recombinant construct including an isolated nucleic acid sequence encoding the cytokine, the nucleic acid sequence being operatively linked to one or more transcription control sequences.

According to further features in preferred embodiments of the invention described below, the autoimmune disease is multiple sclerosis.

According to still further features in the described preferred embodiments the cytokine is a chemokine or tumor necrosis factor alpha.

According to still further features in the described preferred embodiments the chemokine is a C-C chemokine.

According to still further features in the described preferred embodiments the C-C chemokine is selected from the group consisting of macrophage inflammatory protein-1α (MIP-1α), monocyte chemoattractant protein 1 (MCP-1), macrophage inflammatory protein-1β (MIP-1β) and regulation on activation normal T expressed and secreted (RANTES).

According to still further features in the described preferred embodiments the transcription control sequences are selected from the group consisting of RSV control sequences, CMV control sequences, retroviral LTR sequences, SV-40 control sequences and β-actin control sequences.

According to still further features in the described preferred embodiments the recombinant construct is an eukaryotic expression vector.

According to still further features in the described preferred embodiments the recombinant construct is selected from the group consisting of pcDNA3, pcDNA3.1(+/−), pZeoSV2(+/−), pSecTag2, pDisplay, pEF/myc/cyto, pCMV/myc/cyto, pCR3.1, pCI, pBK-RSV, pBK-CMV, pTRES and their derivatives.

According to still further features in the described preferred embodiments the mammal is selected from the group consisting of humans, dogs, cats, sheep, cattle, horses and pigs.

The present invention successfully addresses the shortcomings of the presently known configurations by providing novel means to combat the incurable and poorly treatable disease—multiple sclerosis—devoid of the limitations associated with protective immunity via administered antibodies.

BRIEF DESCRIPTION OF THE DRAWINGS

The invention herein described, by way of example only, with reference to the accompanying drawings, wherein:

FIG. 1b shows a representative Southern blot analysis of each time point. Rats were immunized with p68–86/CFA and developed active EAE (FIG. 1c). Before the induction of disease (day 0), and at various time points: before the onset of disease (day 8), at the peak (day 13) and 5 days after recovery (day 21) mid-brain and brain stem samples from six different rats at each time point, were obtained and subjected to RT-PCR as described above. FIG. 1d shows a representative Southern blot analysis from each time point.

DESCRIPTION OF THE PREFERRED EMBODIMENTS

Figure 1A:
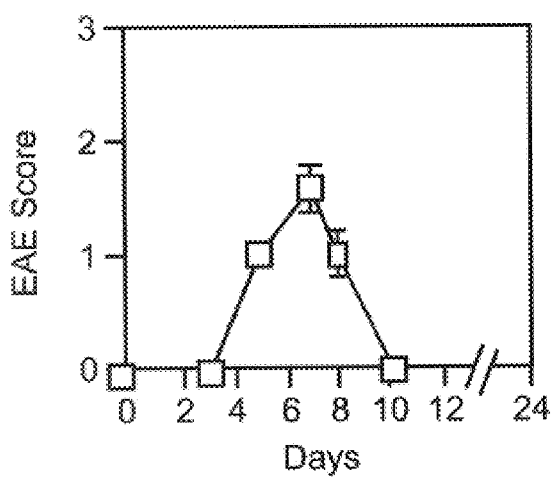
FIGS. 1a–d show the dynamics of mRNA transcription of various C-C chemokines in inflamed brains. Rats were injected with $10^7$ L68–86 cells to develop transferred EAE (FIG. 1a). Before adoptive transfer of disease (day 0), and at various time points: before the onset of disease (day 3), at the day of onset (day 5), the peak (day 7), following recovery (day 10), and 10 days after recovery (day 20) mid-brain and brain stem samples from six different rats at each time point were examined. mRNA was isolated from each sample and subjected to RT-PCR analysis using specific oligonucleotide primers constructed to RANTES, MIP-1α, MIP-1β and MCP-1. Each amplification was, calibrated to β-actin and verified by Southern bolting analygig

The present invention is of DNA vaccines and the use of same to induce protective immunity against autoimmune diseases in mammals. Specifically, the present invention can be used to induce protective immunity against multiple sclerosis by vaccinating with DNA encoding, cytokines, C-C chemokines and tumor necrosis factor alpha in particular.

The principles and operation of the vaccines according to the present invention may be better understood with reference to the drawings and accompanying descriptions.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

An ideal way of treating a disease caused by a malfunction of the immune system in distinguishing self from foreign, would be by encouraging this system to elicit self protective immunity and thus restrain its own harmful reactivity to times when such a response is needed. This task has been achieved in the current study using the novel technology of DNA vaccination.

We have previously used RT-PCR verified by Southern blotting analysis to follow the trafficking of T cells to the site of inflammation is during the course of transferred EAE and distinguished between selective and non-selective stages in leukocyte homing to the CNS (3). Based on these data we have described the development of EAE as a sequential event in which a primary influx (days 0–2) activates the blood brain barrier to allow accumulation of a secondary influx of endogenous leukocytes and the initiation of the disease (days 5–9) (3). Using the same experimental system and the same strategy we now show, in one aspect, a positive correlation in time course between the accumulation of the secondary influx at the site of inflammation (3) and an elevated expression of MIP-1α, MCP-1 and MIP-1β at the site of inflammation. Each of the above C-C chemokines is well known for its competence to attract monocytes and T cells to a site of inflammation and for its ability to elicit the expression of various adhesion molecules that mediate the trafficking of these cells (3). Thus, the positive correlation in time course between chemokine expression and cell accumulation at the target organ may be explicated by the putative biological functions of these chemokines. Unexpectedly, RANTES transcription augmented in EAE brains only after recovery. While similar results were previously obtained in a murine model of the disease (40), the biological implications of this observation are not fully understood.

As detailed in the Examples section hereinunder, MIP-1α a or MCP-1 DNA vaccines prevented EAE. MIP-1 β naked DNA significantly aggravated the disease, whereas the generation of in vivo immune response to RANTES naked DNA had no notable effect on EAE manifestation. Thus, intervention in EAE development by C-C chemokine DNA vaccines was effective only for those chemokines which were highly transcribed during the development of the inflammation. This emphasizes the pivotal role of these chemokines in the pathogenesis of EAE. It is possible that RANTES plays a role in the establishment and maintenance of the resistant state following recovery.

DNA vaccines represent a novel means of expressing antigens in vivo for the generation of both humoral and cellular immune responses (10, 14, 41–43) This technology has proven successful in obtaining immunity not only to foreign antigens and tumors, but also to self antigens, such as a T cell receptor V genes (17) or autologous cytokines (42). C-C chemokines were selected as candidates for DNA vaccination mostly because of their well established role in cell migration to a target organ (22, 23, 44–49). Since DNA vaccination elicits both cellular and humoral responses against products of a given construct (10, 14, 41–43), it is difficult to know which of these responses contributed more to the development of EAE resistance in MCP-1 and MIP-1α DNA vaccinated rats. It has, however, been shown that rabbit anti-MIP-1α antibodies were capable of blocking EAE in a murine model (33), and an antagonist of MCP-1 markedly inhibited arthritis in the MRL-1pr mouse (34). Under our experimental conditions, vaccination with MCP-1 DNA elicited a significant cross-reactive immune response to MIP-1α. Our data clearly show that anti-chemokine antibodies produced by naked DNA vaccination are neutralizing antibodies and can is provide subsequent protection from severe EAE. Thus, it conceivable that these antibodies contributes to disease inhibition by in MIP-1α and MCP-1 naked DNA vaccinated rats, As already mentioned in the Background section hereinabove, a major disadvantage in treating chronic diseases with xenogenic neutralizing antibodies lies in their immunogenicity.

The therapeutic strategy suggested herein, is of advantage over the above methods since it resulted in the generation of immunity to autologous antigens. In addition, the data presented herein reveals an unexpected, yet extremely important, advantage in applying C-C chemokine DNA vaccmnation. It appears that the immune response to each of the given DNA constructs elicited only during the course of disease and only at the time when the transcription of the related chemokine profoundly elicited at the gite of inflammation EAE induction.

Finally, a recent study shows a coordinated chemokine up-regulation in brain and spinal cord during clinical relapse in mice with relapsing EAE (52). This emphasizes the importance of treating a disease caused by a malfunction of the immune system in distinguishing self from foreign, such as multiple sclerosis, by encouraging this system to elicit anti-self protective immunity and thus restrain its own harmful only when such a response is needed.

In the process of negative selection in the thymus many, but not all, self reactive T cells are eliminated. Autoreactive T cells that escape thymic selection can be identified in both healthy individuals and those suffering form self destructive autoimmune diseases (72). In healthy individuals self tolerance is maintained in part through mechanisms acting outside the thymus that keep these autoreactive lymphocytes under control. Anti inflammatory cytokines such as TGF-β, IL-10, IL-4 and IL-13 produced by antigen specific regulatory T cells and macrophageg are involved in restraining the activity of autoreactive T cells, and for keeping the tolerant state under control (73–82).

In another aspect, the present invention demonstrates, for the first time, the appearance of 'natural' anti self antibodies to a key proinflammatory cytokine, TNF-α, during the development of a T cell mediated autoimmune disease of the central nervous system. These antibodies were developed in rats immunized with p68–86/CFA and not with the CFA alone even though both groups exhibited an extensive local inflammatory process at the site of CFA immunization. Thus, only the transcription of the inflammatory cytokine TNF-α at an privileged autoimmune site (CNS) enabled the triggering of an anti-self response against this pro-inflammatory cytokine.

The biological significance of these results is apparent. An ideal immune system would be evolutionary selected to centralize its destructive competence against invading microbes rather than the self tissues its was designed to protect (83–85). The underlying mechanism by which the immune system distinguishes a gene products transcribed at a privileged autoimmune site from the same gene product transcribed at a local site of inflammation is, however elusive. A partial explanation has been previously suggested by C. C. Goodnow and his colleagues who demonstrated that peripheral clonal exclusion of self reactive B cells occurs at germinal centers of lymph nodes that drain tissues lacking immune prevalence, where competition for follicular niches do not exclude self reactive cells from the recalculating B cell repertoire (86). The 'natural' anti self production to TNF-α in EAE susceptible rats was, however, not sufficient to prevent the development of an autoimmune condition (6/6 sick rats).

An ideal way of treating a disease caused by a malfunction of the immune system in distinguishing self from foreign would be by encouraging this system to elicit self protective immunity and thus restrain its own harmful reactivity only when such a response is needed. This task has been achieved according to the present invention using the novel technology of naked DNA vaccination. DNA vaccines represent a novel means of expressing antigens in vivo for the generation of both humoral and cellular immune responses (10, 14, 41–43). This technology has proven successful in obtaining immunity not only to foreign antigens and tumors, but also to self antigens, such as a T cell receptor V genes (17) or autologous cytokines (42). Since DNA vaccination elicits both cellular and humoral responses against products of a given construct (10, 14, 41–43), it is difficult to know which of these responses contributed more to the development of EAE resistance in TNF-α DNA vaccinated rats. The data showing that TNF-α specific self antibodies produced by naked DNA vaccination can provide subsequent protection from severe EAE votes for there pivotal role in the prevention of EAE. The mechanism by which TNF-α specific naked DNA vaccines augment production of anti-self neutralizing antibodies is not fully addressed yet. The possibility that naked DNA vaccination elicits the activation of self reactive T cells that help production of autoreactive antibodies to TNF-α when this cytokine is profoundly transcribed at an autoimmune privileged area is not excluded.

As already mentioned, from a clinical perspective, however, a major disadvantage in treating chronic diseases with xenogenic neutralizing antibodies lies in their immunogenicity. This has motivated investigators to develop chimeric humanized antibodies (reviewed in (50)), and monoclonal antibodies engineered with human Ig heavy and light chain yeast artificial chromosome (YAC) (51). However, following repeated immunization, these engineered antibodies do trigger an apparently allotypic response. The therapeutic strategy suggested by the present invention, is of advantage over the above methods since it resulted in the generation of immunity to autologous antigen only during the course of disease at the time when the transcription of the proinflammatory cytokine profoundly elicited at the site of inflammation.

Thus, in accordance with one aspect of the present invention, there is provided a method for treating a mammal for inducing protective immunity against an autoimmune disease. According to the method, a mammal is administered with a therapeutic composition including a recombinant construct including an isolated nucleic acid sequence encoding a cytokine, the nucleic acid sequence being operatively linked to one or more transcription control sequences.

As used herein in the specification and in the claims section below, the phrase "inducing protective immunity" refers to eliciting neutralizing antibodies via DNA vaccination.

As used herein in the specification and in the claims section below, the phrase "autoimmune disease" refers to a disease resulting from a disordered immune reaction in which antibodies are produced that damage components of one's own body.

As used herein in the specification and in the claims section below, the terms "cytokine" and "chemokine" also refer to therapeutically effective potions of cytokines and chemokines, i,e., portions that are effective in eliciting the described protective immunity.

Thus, in accordance with another aspect of the present invention, there is provided a method for treating a mammal for inducing protective immunity against an autoimmune disease. The method according to this aspect of the invention is effected by executing the following method steps, in which, in a first step, cells are removed of the mammal, in a second step, the cells are transduced in vitro with a recombinant construct including an isolated nucleic acid sequence encoding a cytokine, the nucleic acid sequence being operatively linked to one or more transcription control sequences, whereas in a third step, the transduced cells are reintroduced to the mammal.

As used herein in the specification and in the claims section below, the term "transduced" or "transducing" refers to the result of a process of inserting nucleic acids into cells. The insertion may, for example, be effected by transformation, viral infection, injection, transfection, gene bombardment, electroporation or any other means effective in introducing nucleic acids into cells. Following transduction the nucleic acid is either integrated in all or part, to the cell's genome (DNA), or remains external to the cell's genome, thereby providing stably transduced or transiently transduced cells.

The cells according to this method may be of any kind. Especially suitable cells are those readily removable, tranduceable, and reintroduceable cells, such as, but not limited to, cells of the various blood lineage, derived either from whole blood or bone marrow, fibroblast cells, etc. The transduced cells are preferably reintroduced to the mammal parenterally.

According to yet another aspect of the present invention there is provided a pharmaceutical composition suitable for effecting the above methods of the present invention. The composition includes a recombinant construct including an isolated nucleic acid sequence encoding a cytokine, the nucleic acid sequence being operatively linked to one or more transcription control sequences, and a pharmaceutically acceptable carrier.

The pharmaceutically acceptable carrier may be of any acceptable form. Examples include, but are not limited to, aqueous physiologically balanced solutions, artificial lipid-containing substrates, natural lipid-containing substrates, oils, esters, glycol, viruses and metal particles.

The composition is preferably made suitable for parenteral administration to a human. It is therefore preferably sterile (except for infective particles, if deliberately present therein) and may additionally include adjuvant allowed for use in human beings, such as Bacillus Calmette Guerein (BCG) including adjuvant.

According to one embodiment of the present invention, the pharmaceutically acceptable carrier includes a delivery vehicle that delivers the nucleic acid sequences to the mammal. Suitable delivery vehicles include, but are not limited to, liposomes, micelles, and cells.

The construction, operation and use of the above pharmaceutically acceptable carriers for DNA vaccination and the above delivery vehicles are described in detail in U.S. Pat. No. 5,705,151 to Dow et al., entitled "gene therapy for T cell regulation", which is directed at anti-cancer treatment, and is hereby incorporated by reference as if fully set forth herein.

Thus, for therapeutic or prophylactic treatment, the composition according to the present invention may include thickeners, carriers, buffers, diluents, surface active agents, preservatives, and the like, all as well known in the art. Pharmaceutical compositions may also include one or more active ingredients, such as , but not limited to, anti-inflammatory agents, anti-microbial agents, anesthetics and the like.

The pharmaceutical composition may be administered in either one or more of ways. Administration may be effected topically (including ophtalmically, vaginally, rectally, intranasally), orally, by inhalation, or parenterally, for example by intravenous drip or intraperitoneal, subcutaneous, or intramuscular injection.

Formulations for topical administration may include but are not limited to lotions, ointments, gels, creams, suppositories, drops, liquids, sprays and powders. Conventional pharmaceutical carriers, aqueous, powder or oily bases, thickeners and the like may be necessary or desirable.

Formulations for parenteral administration may include but are not limited to sterile aqueous solutions which may also contain buffers, diluents and other suitable additives.

Dosing is dependent on responsiveness, but will normally be one or more doses per week or month, with course of treatment lasting from several weeks to several months. Persons ordinarily skilled in the art can easily determine optimum dosages, dosing methodologies and repetition rates.

According to yet another aspect of the present invention there is provided an antibody raised against a cytokine expressed by cells transduced with a recombinant construct including an isolated nucleic acid sequence encoding the cytokine, the nucleic acid sequence being operatively linked to one or more transcription control sequences.

As used herein in the specification and in the claims section below, the term "antibody" refers to any monoclonal or polyclonal immunoglobulin, or a fragment of an immunoglobulin such as sFv (single chain antigen binding protein), Fab1 or Fab2. The immunoglobulin could also be a "humanized" antibody, in which murine variable regions are fused to human constant regions, or in which murine complementarity-determining regions are grafted onto a human antibody structure (Wilder, R. B. et al., J. Clin. Oncol., 14:1383–1400, 1996). The terms "sFv" and "single chain antigen binding protein" refer to a type of a fragment of an immunoglobulin, an example of which is sFv CC49 (Larson, S.M. et al., Cancer, 80:2458–68, 1997).

As further exemplified in the Examples section hereinunder, the methods, compositions and antibodies according to the present invention are useful at inducing protective immunity against autoimmune diseases, multiple sclerosis, in particular.

According to a preferred embodiment of the present invention the nucleic acid sequence selected encodes a chemokine, in particular a C-C chemokine, most particularly inflammatory protein-1α (MIP-1α), monocyte chemoattractant protein 1 (MCP-1), macrophage inflammatory protein-1β (MIP-1β) and/or regulation on activation normal T expressed and secreted (RANTES). Any combination of sequences encoding cytokines may be simultaneously employed according to the present invention on different or single constructs. According to another embodiment the nucleic acid sequence selected encodes tumor necrosis factor alpha.

The transcription control sequences may be of any suitable type compatible with eukaryotic gene expression. Strong and effective control sequences are preferably of choice. These sequences can be from a mammalian or viral source. Examples include, but are not limited to, RSV control sequences, CMV control sequences, retroviral LTR sequences, SV-40 control sequences and β-actin control sequences, all of which are potent and effective control sequences, capable of efficiently directing gene expression.

According to a preferred embodiment of the present invention the recombinant construct is an eukaryotic expression vector, such as, but not limited to, pcDNA3, pcDNA3.1 (+/−), pZeoSV2(+/−), pSecTag2, pDisplay, pEF/myc/cyto, pCMV/myc/cyto, pCR3.1, which are available from Invitrogen, pCI which is available from Promega, pBK-RSV and pBK-CMV which are available from Stratagene, pTRES which is available from Clontech, and their derivatives.

The present invention is suitable for prevention autoimmune diseases in any mammal. Examples include, but are not limited to, humans, dogs, cats, sheep, cattle, horses and pigs.

EXAMPLES

Reference is now made to the following examples, which together with the above descriptions, illustrate the invention in a non limiting fashion.

MATERIALS AND EXPERIMENTAL METHODS

Rats: Female Lewis rats, approximately six weeks old were purchased from Harlan (Israel) and maintained under SPF conditions in an animal facility.

Peptide antigens: Myelin basic protein (MBP) p68–86, YGSLPQKSQRSQDENPV (SEQ ID NO:1), was synthesized on a MilliGen 9050 peptide synthesizer by standard 9-fluorenylmethoxycarbonyl chemistry. Peptides were purified by high performance liquid chromatography. Structure was confirmed by amino acid analysis and mass spectroscopy. Only peptides that were greater than 95% pure were further used.

Immunizations and active disease induction: Rats were immunized subcutaneously in the hind foot pads with 0.1 ml of MBP epitope 68–86 (p68–86) dissolved in phosphate buffer saline (PBS, 1.5 mg/ml) and emulsified with an equal volume of CFA (incomplete Freund's adjuvant supplemented with 4 mg/ml heat-killed *Mycobacterium tuberculosis* H37Ra in oil (Difco laboratories, Inc., Detroit, Mich.). Rats were then monitored for clinical signs daily by an observer blind to the treatment protocol. EAE was scored as follows: 0, clinically normal; 1, flaccid tail; 2, hind limb paralysis; 3, front and hind limb paralysis.

T-cell lines: Nine days after induction of active EAE, draining lymph node cells (DLNC) were cultured ($12\times10^6$/ml) for three days in stimulation medium that includes Dulbecco's modified Eagle's medium (Gibco BRL) supplemented with β-mercaptoethanol ($5\times10^{-5}$ M), L-glutamine (2 mM), sodium pyruvate (1 mM), penicillin (100 µg/ml) streptomycin (100 µg/ml), 1% syngeneic serum and 20–30 µg/ml of the immunizing epitope, washed and resuspended in resting medium which was identical to the stimulation medium without Syngeneic serum and with the addition of 10% fetal calf serum (Gibco BRL) and 12.5% supernatant of Con A stimulated splenocytes as a source of T cell growth factors. Con A supernatant was prepared as described elsewhere (36). After five-seven days in resting medium the cells ($5\times10^5$/ml) were activated for three days in the presence of irradiated (2500R) syngeneic thymocytes ($12\times10^6$/ml) and 10–20 µg/ml of p68–86. The activated T cells were then either used for induction of transferred EAE or resuspended in resting medium for additional growing cycles.

Induction of transferred EAE: Transferred EAE was induced by immunizing Lewis rats (intraperitoneally) with $10^7$ in vitro activated (day 3) L68–86 cells.

Reverse transcriptase polymerase chain reaction (RT-PCR) analysis: RT-PCR analysis, verified by Southern blotting, was utilized on brain samples according to a protocol described elsewhere with some modifications (3). Rats were euthanized by $CO_2$ narcosis. Brain samples containing mainly the midbrain and brain stem were obtained after perfusion of the rat with 160–180 ml of ice-cold phosphate buffer saline (PBS) injected into the left ventricle following an incision in the right atrium. Each sample was homogenized. Total RNA was extracted using the Tri-Zol procedure (Gibco BRL) according to the manufacturer's protocol. mRNA was then isolated using a mRNA isolation kit (#1741985 Boheringer Mannheim, Germany), and reverse transcribed into first strand cDNA exactly as is describe in detail elsewhere (3). First strand cDNA was then subjected to 35 cycles of PCR amplification using specific oligonucleotide primers which were designed based on the published sequence of each cytokine (NCBI accession numbers Rat MIP-1α U06435, Rat MIP-1β U06434, Rat RANTFS U06436 and Rat MCP-1 M57441, Rat TNF-α L00981, which sequences are incorporated by reference as if fully set forth herein) as follows: MIP-1α sense: 5'-ATGAAGGTCTCCACCACTGCCCTTGC-3' (SEQ ID NO:2); MIP-1αantisense: 5'-TCAGGCATTCAGTTCCAGCTCAGTG-3' (SEQ ID NO:3); MIP-1β sense: 5'-ATGAAGCTCTGCGTGTCTGCCTTC-3' (SEQ NO;4); MIP-1β antisense: 5'-TCAGTTCAACTCCAAGTCATTCAC-3' (SEQ ID NO:5); RANTES sense: 5'-ATGAAGATCTCTGCAGCTGCATCC-3' (SEQ ID NO:6); RANTES antisense: 5'-CTAGCTCATCTCCAAATAGTTG-3' (SEQ ID NO:7); MCP-1 sense: 5'-ATGCAGGTCTCTGTCACGCTTCTGGGC-3' (SEQ ID NO:8); MCP-1 antisense: 5'-CTAGTTCTCTGTCATACTGGTCAC-3' (SEQ ID NO:9); TNF-α sense: 5'-ATGAGCACAGAAAGCATGAT-3' (SEQ ID NO:10); and TNF-α antisense: 5'-TCACAGAGCAATGACTCCAAA-3' (SEQ ID NO: 11).

All RNA samples were calibrated to Rat β-actin: β-actin sense 5'-CATCGTGGGCCGCTCTAGGCA-3' (SEQ ID NO: 11); and β-actin antisense: 5'-CCGGCCAGCCAAGTCCAGACG-3' (SEQ ID NO: 12).

The cycle profile was: denaturation at 95° C. for 60 sec, annealing at 55° C. for 60 sec, and elongation at 72° C. for 60 sec.

Amplified products were subjected to agarose gel electrophoresis, transferred to a nylon membranes (MagnaGraph nylon transfer membrane, msi, Westborough, Mass.), fixed with ultraviolet light (120 mjoules) and hybridized with $10^6$ cpm/ml of $\alpha^{32}P$ labeled DNA fragments encoding the full length PCR product of each cytokine and of β-actin (random priming: Amersham, Arlington Heights, Ill.). PCR products were used as probes only after each PCR product was cloned and its sequence was verified as further described hereinunder.

Cloning and sequencing of PCR products: Each of the amplified PCR products described above was cloned into a pUC57/T vector (T-cloning Kit #K1212, MBI Fermentas, Lithuania) and transformed to *E. coli* according to the manufacturer's protocol. Each clone was then sequenced (Sequenase version 2, USB, Cleveland, Ohio) according to the manufacturer's protocol. PCR products were selected to be used as constructs for naked DNA vaccination only after cloning and sequence verification.

DNA vaccination: DNA vaccination was performed according to Waisman at al. with some modifications (17).

Sequenced PCR products of rat MIP-1α, MCP-1, MIP-1β, RANTES and TNI-α were transferred into a pcDNA3 vector (Invitrogen, San Diego, Calif.). Large scale preparation of plasmid DNA was conducted using Mega prep (Qiagen Inc., Chatsworth, Calif.). Cardiotoxin (Sigma, St. Louis, Mo.) was injected into the tibialis anterior muscle of 6–8 weeks old female Lewis rats (10 μM per leg). One week following injection rats were injected with 100 μg DNA in PBS. Four-five days after the first immunization one rat from each group was sacrificed and transcription of the relevant chemokine was verified using RT-PCR on tibialis anterior muscle samples, Thereafter, naked DNA vaccines were given 3–5 times with intervals of 6–7 days between each injection.

Production and purification of recombinant proteins: PCR products were recloned into a PQE expression vector (PQE30, PQE-31 or PQE-32 according the correct open reading frame) and were expressed in E. Colti (Qaigen, Chatsworth, Calif.) and then purified by a NI-NTA-supper flow affinity purification of 6xHis proteins (Qaigen, Chatsworth, Calif.). Each recombinant protein sequence has then been verified (N-terminus) by the AB1494 Sequencer (Applied Biosystem Division, Perkin Elmer).

Purinfcation of antibodies: Antibodies from rat sera were purified using a High-Trap Protein G column (Pharmacia, Piscataway, N.J.) according the manufacturer's protocol. Then antibody titer to various chemokines was determined by an ELISA assay as described bellow.

In vitro chemotaxis assay: In vitro chemotaxis assay was conducted as previously described (37) with minor modifications according to (38). Peritoneal macrophages were isolated as previously described (38) and suspended in DMEM enriched with 1% BSA. Cell migration was evaluated in standard Boyden chambers (Neuroprobe, Cabin John, Md.). Macrophages ($1.2 \times 10^6$ cells) were added to the upper well. Chemotactic factors: fMLP (Sigma, $10-7$ M), rat recombinant MIP-1α(Chemicon International, Temecula, Calif., 200 ng/ml) or rat recombinant MCP-1 (Chemicon International, Temecula, Calif., 100 ng/ml) were added to the lower wells, with, or without pre-incubation with the required antibodies (10 μg/well) at 37° C. for 30 minutes. Migration was allowed to proceed for 90 minute at 37° C. The celloulose nitrate filters (5 μm pore size) were then fixed and stained as described (37). Five×400 fields were selected randomly on each filter and the migrating cells were counted.

Evaluation of anti-chemokine antibody titer in sera of DNA vaccinated raise. A direct ELISA assay was utilized to determine the anti-C-C chemokine antibody titer in DNA vaccinated rats. Each recombinant chemokine which was produced, as well as commercial recombinant rat RANTES, rat MIP-1α, rat MCP-1, human MIP-1β (Chemicon International, Temecula, Calif.) and rat TNF-α (Geryyme, Cambridge, Mass.) were coated onto 96 well ELISA plates (Nunc, Denmark), at concentrations of 50 ng/well. Rat anti-sera, in serial dilutions from $2^8$ to $2^{30}$ were added to ELISA plates coated with each recombinant chemokine. Goat anti-rat IgG alkaline phosphatase conjugated antibodies (Sigma) were used as a labeled antibody. p-Nitrophenyl Phosphate (p-NPP, Sigma) was used as a soluble alkaline phosphatase substrate. The assay conditions and data calculation of each test were done according to (14). Results are shown as $\log_2$ antibody titer±SE. Commercial monoclonal antibodies to each cytokine (Chemicon International) were used as a positive control for detected sera in each experiment.

Histopathology: Histological examinations of hematoxylin and eosin-stained sections of formalin-fixed, paraffin-embedded sections of brain and the lower thoracic and lumbar regions of the spinal cord were performed. Each section was evaluated without knowledge of the treatment status of the animal. The following scale was used: 0, no mononuclear cell infiltration; 1, 1 to 5 perivascular lesions per section with minimal parenchymal infiltration; 2, 5 to 10 perivascular lesions per section with parenchymal infiltration; and 3, >10 perivascular lesions per section with extensive parenchymal infiltration. The mean histological score±SE was calculated for each treatment group. Representative photomicrograph are shown in FIGS. 3a–g.

Antigen-specific T cell proliferation assays. Lewis rats were immunized with MBP p68–86/CFA as described above. Nine to ten days later spleen cells were suspended in stimulation medium and cultured in U-shape 96-well microculture plates ($2 \times 10^5$ cells/well) for 72 hours, at 37° C. in humidified air containing 7.5% $CO_2$. Each well was pulsed with 2 μCi of [$^3$H]-Thymidine (specific activity 10 Ci/mmol) for the final six hours. The cultures were then harvested on fiberglass filters and the proliferative response expressed as CPM±SD or as stimulation index (SI) (mean CPM of test cultures divided by mean CPM of control cultures).

Cytokine determination. Spleen cells from EAE donors were stimulated in vitro ($10^7$ cells/ml) in 24 well plates (Nunc) with 100 μM p68–86. After 72 hours of stimulation, supernatants were assayed by semi-ELISA kits, that include antibody pairs and recombinant rat cytokines, as follows: IFN-γ, rabbit anti-rat IFN-γ polyclonal antibody (CY-048, Innogenetics, Belgium) as a capture antibody, biotinylated mouse anti-rat monoclonal antibody (CY-106 clone BD-1, Innogenetics) as a detection antibody, and Alkaline phosphatase-Streptavidin (cat No. 43-4322, Zymed, SF, CA) with rat recombinant IFN-γ as a standard (Cat. No. 3281SA, Gibco BRL); TNF-α, commercial semi-ELISA kit for the detection of rat TNF-α, (Cat. No. 80-3807-00, Genzyme, Cambridge, Mass.); IL-4, mouse anti-rat IL-4 monoclonal antibody (24050D OX-81, PharMingen, San Diego, Calif.) as a capture antibody, and rabbit anti-rat IL-4 biotin-conjugated polyclonal antibody (2411-2D, PharMingen) as second antibody. Recombinant rat IL-4 purchased from R&D (504-RL) was used as a standard.

Figure 10:
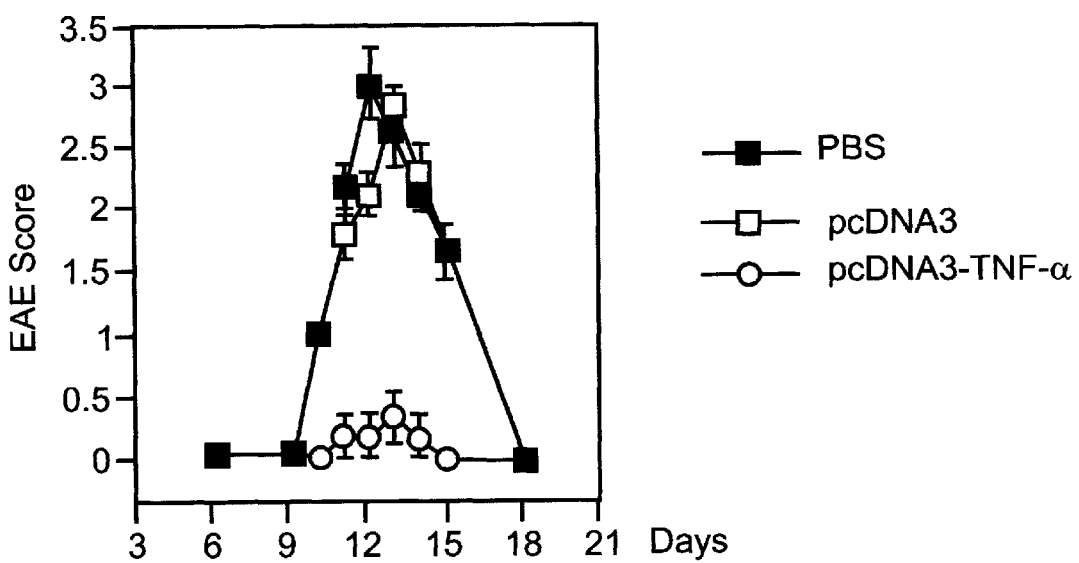
FIG. 10 shows prevention against EAE using TNF-α naked DNA vaccine. Rats were immunized weekly with the cloned PCR products of TNF-α ligated into a pcDNA3 eukaryotic expression vector, or with the pcDNA3 sector alone, or with PBS. Two months after the last immunization all rats were immunized with p68–86/CFA to induce active EAE and were monitored for clinical signs daily by an observer blind to the treatment protocol. EAE wag scored as follows: 0, clinically normal; 1, flaccid tail; 2, hind limb paralysis; 3, front and hind limb paralysis. Results are shown as mean clinical score of six rats in each group±SE.

Statistical analysis. Significance of differences was examined using Student's t-test (FIGS. 2, 4, 5, 9, 10, 11 and 12). A value of $p<0.05$ was considered significant. One way multiple range ANOVA test with significance level of $p<0.05$ was performed for multiple compression of antibody titer to various chemokines in naked DNA vaccinated rats (FIGS. 4a–d, and 6a–d). Mann-Whitney sum of ranks test was used to evaluate significance of differences in mean of maximal clinical score (FIG. 10). Value of $P<0.05$ was considered significant.

Experimental Results

Figure 1C:
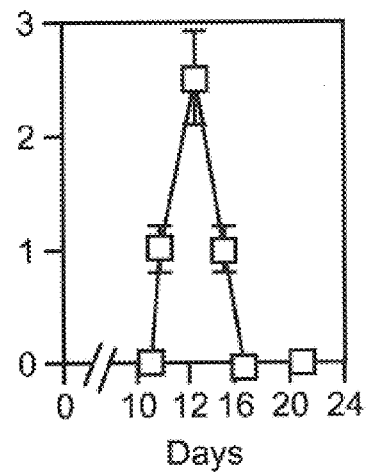
Figure 1B:
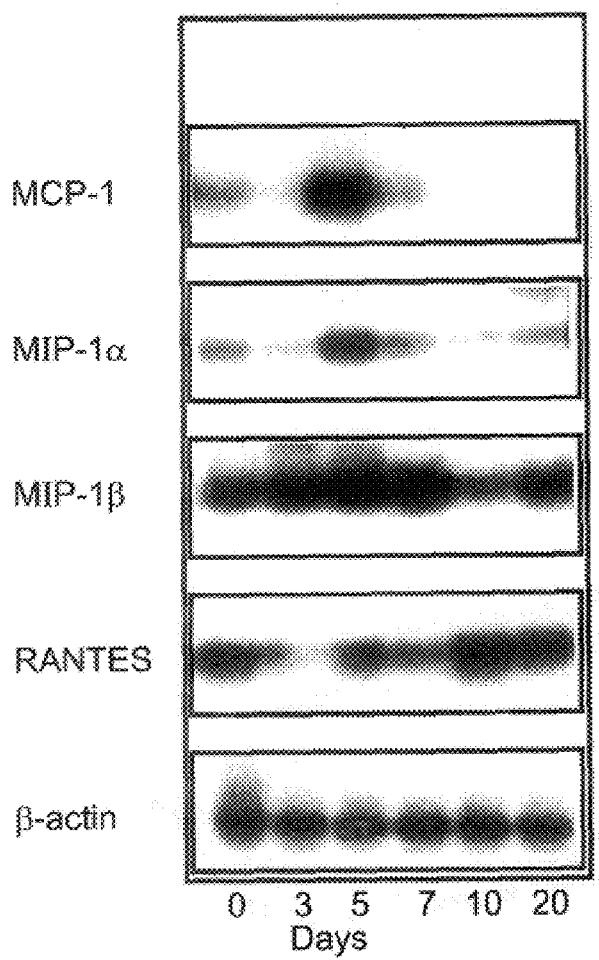
Figure 1D:
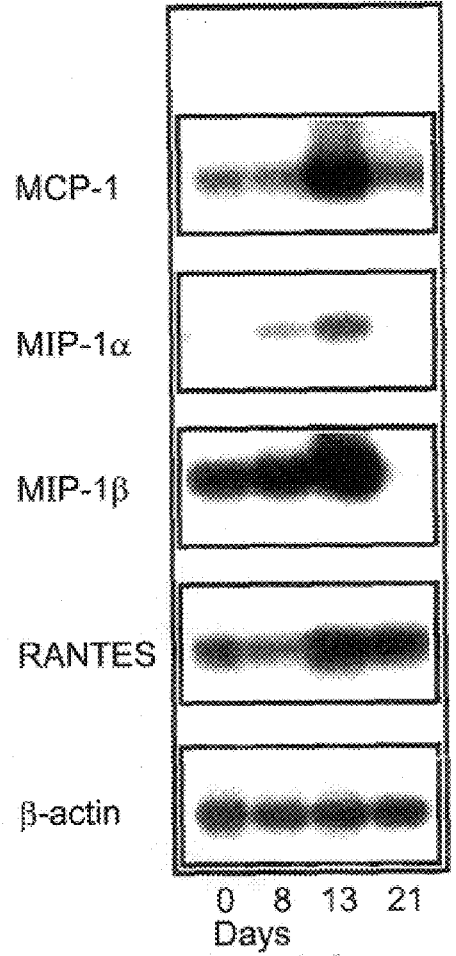

Dynamics of transcription of various C-C chemokine mRNAs in the inflamed brain: Rats injected with L68–86 developed transferred EAE that persisted for 5–6 days (FIG. 1a). Before adoptive transfer of disease (day 0), and at various time points: before the onset of disease (day 3), at the day of onset (day 5), the peak (day 7), following recovery (day 10), and 10 days after recovery (day 20) midbrain-brain stem samples were obtained from six different rats at each time point. From each sample, mRNA was isolated and subjected to RT-PCR analysis using specific oligonucleotide primers which were constructed for each chemokine (SEQ ID NOs:2–9). Each amplification was calibrated to β-actin and verified by Southern blotting analysis. This enabled semi-quantitative analysis of the dynamics of mRNA transcription of each of the above C-C chemokines at the site of inflammation. FIG. 1b shows representative results from each time point of the experiment. An increased transcription of MIP-1α, MCP-1 and MIP-1β mRNA in EAE brains was observed at the onset of disease (day 5). The augmented transcription of MIP-1α and MCP-1 regressed to background within two days even though disease continued to progress to its maximal clinical score on day 7 (FIGS. 1a–b). The increased transcription of MIP-1β, however, declined to its background in correlation with recovery (FIGS. 1a–b). Unexpectedly, RANTES transcription increased in EAE brains only after recovery. The biological significance of this observation remains to be elucidated. Rats with developing active disease manifested similar mDNA transcription characteristics as those with developing transferred disease. That is, an elevated expression of MCP-1, MIP-1α and MIP-1β at the onset of disease which declines during recovery, and an augmented transcription of RANTES following recovery (FIGS. 1c–d).

Figure 2A:
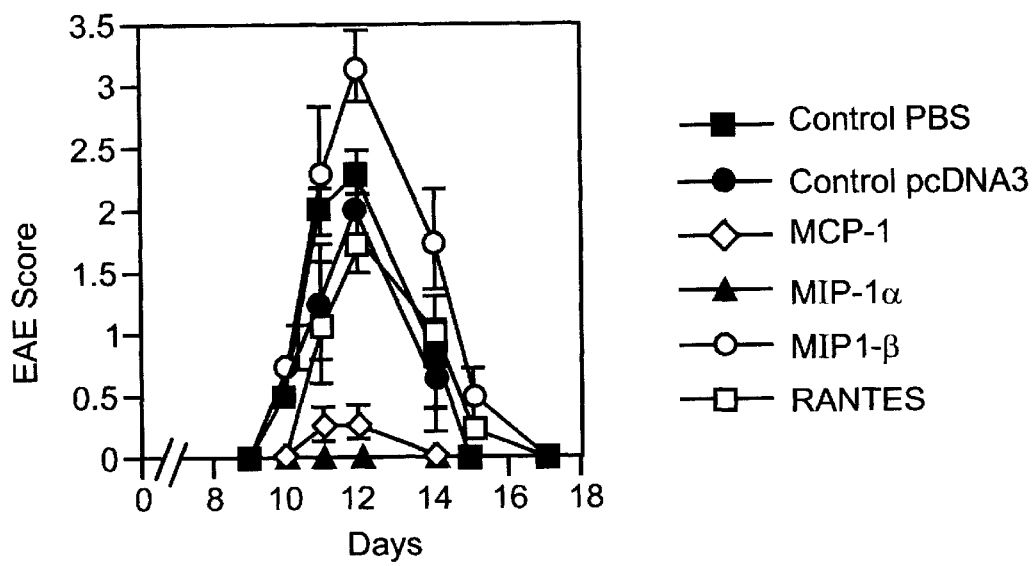
FIGS. 2a–b demonstrate the prevention of EAE using C-C chemokine naked DNA vaccines. Rats were immunized weekly (three repeated immunizations FIG. 2a, five repeated immunizations FIG. 2b) with cloned PCR products of various C-C chemokines ligated into a pcDNA3 eukaryotic expression vector, or with the pcDNA3 vector alone, or with PBS. Two weeks after the last immunization all rats were immunized with p68–86/CFA to induce active EAE. One month after the last immunization all rats were immunized with p68–86/CFA to induce active FAE and monitored for clinical signs daily by an observer blind to the treatment protocol. EAE was scored as follow: 0, clinically normal; 1, flaccid fail; 2, hind limb paralysis; 3, front and hind limb paralysis. Results are shown as mean clinical score of six rats in each group±SE.
Figure 2B:
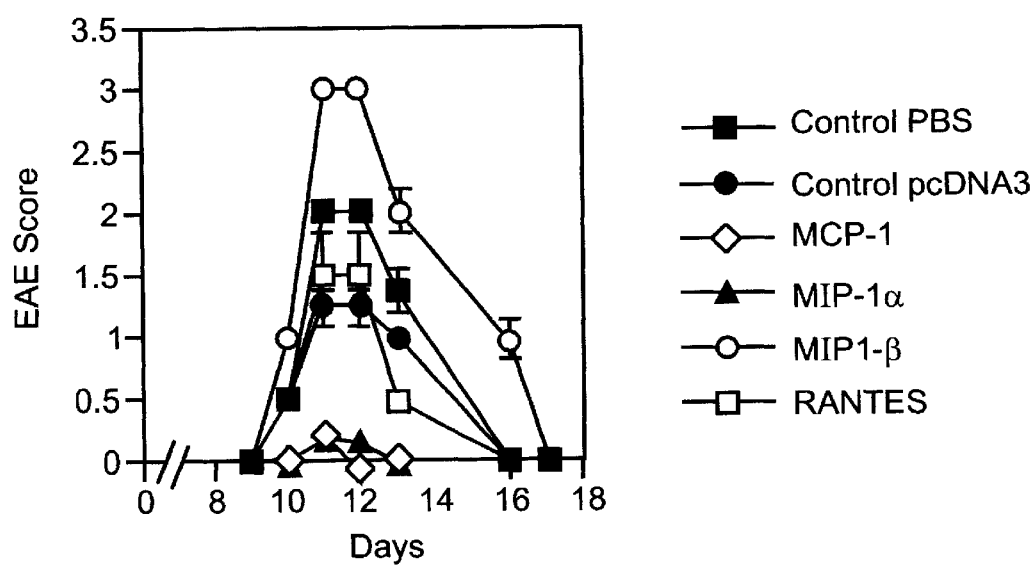
Figure 3A:
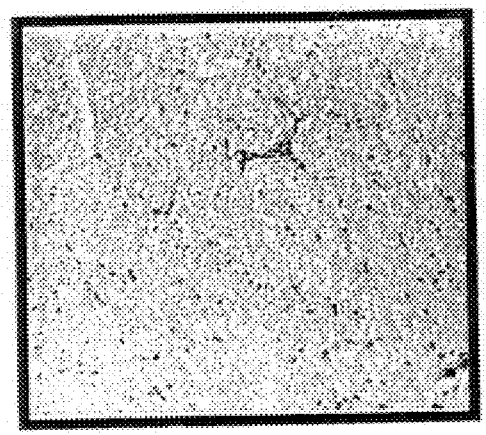
FIGS. 3a–g show that MIP1-α MCP-1 naked DNA vaccines decreases CNS mononuclear cell infiltration. When active EAE attained its maximal clinical severity (day 12, second experiment, FIG. 2b), samples from the lower thoracic and lumbar regions of the spinal cord were histologically evaluated. Histological scores were determined using an 0 to 3 scale as described in the methods. The mean clinical score±SE were calculated from 6 sections per spinal cord of 2 representative rats from each group (see Table 2 below for more details).
Figure 3B:
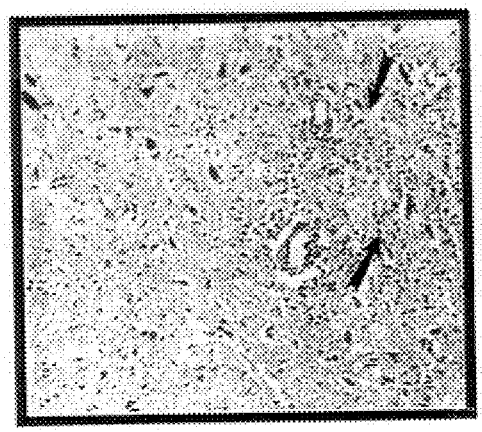
Figure 3C:
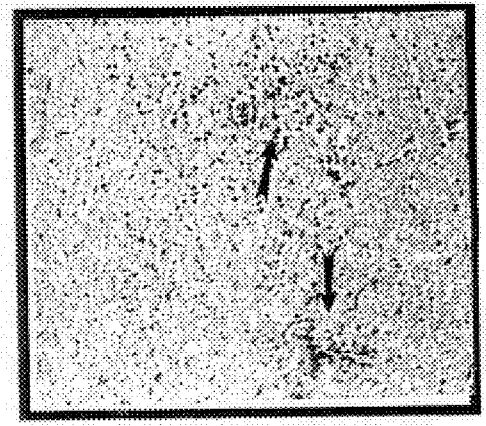
Figure 3D:
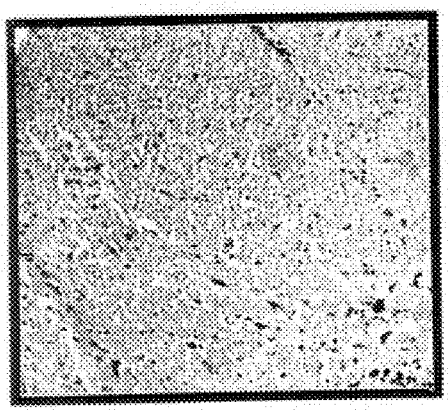
Figure 3E:
Figure 3F:
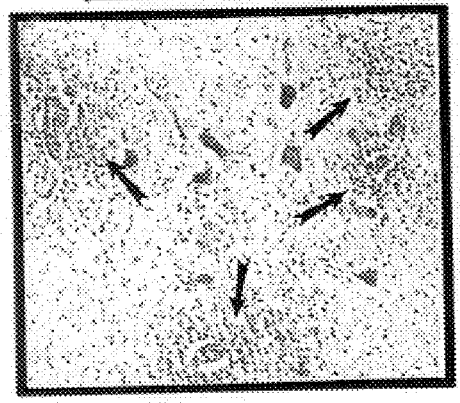
Figure 3G:
Figure 4A:
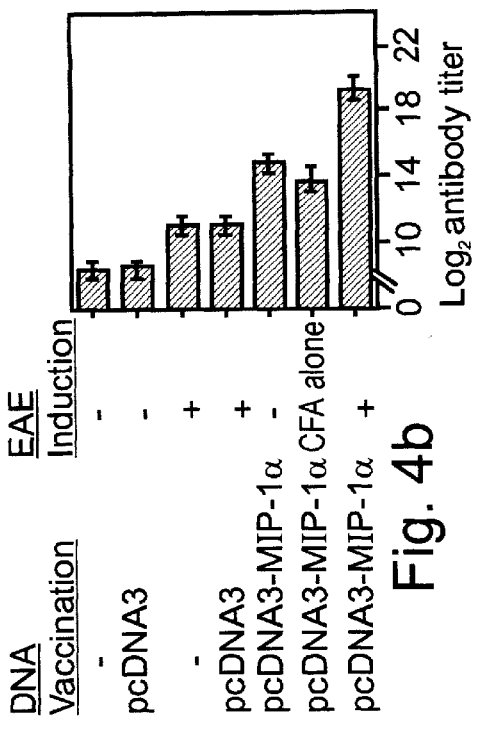
FIGS. 4a–d show synchronic protective immunity to EAE following C-C chemokine naked DNA vaccination. Twelve days after active induction of disease (with p68–86/CFA) sera of rats from the second experiment (FIG. 2b), as well as sera from rats that received the same subsequent set of naked DNA vaccinations, but were finally challenged with the emulsion of PBS and CFA without p68–86, or from rats that received the same subsequent set of naked DNA vaccinations but were never challenged with p68–86/CA or CFA were tested for antibody titer against each of the four C-C chemokines: MCP-1 (FIG. 4a), MIP-1α (FIG. 4b), MIP-1β (FIG. 4c) and RANTES (FIG. 4d). The assay conditions and data calculation of each test was done according to (14). Results are shown as mean log 2 of four different samples±SE.
Figure 4B:
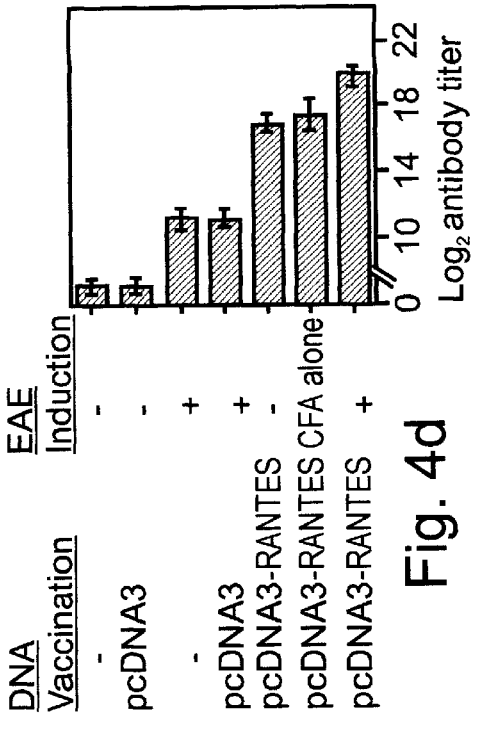
Figure 4C:
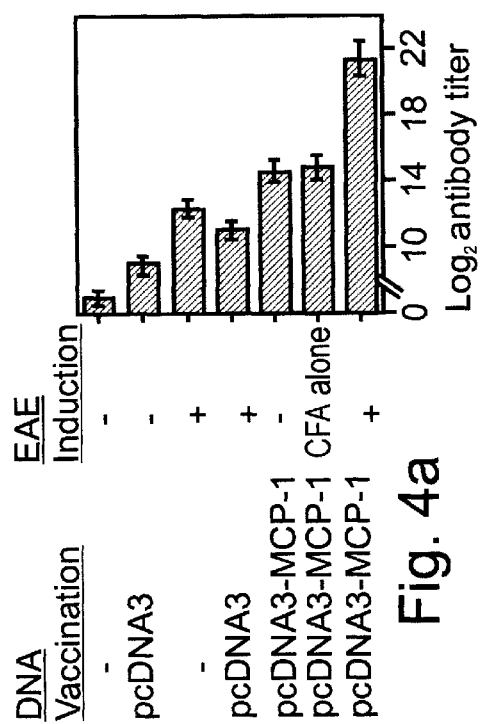
Figure 4D:
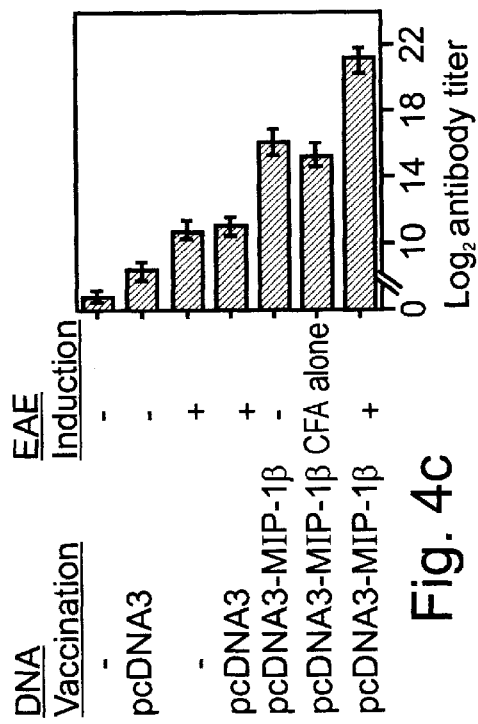
Figure 5A:
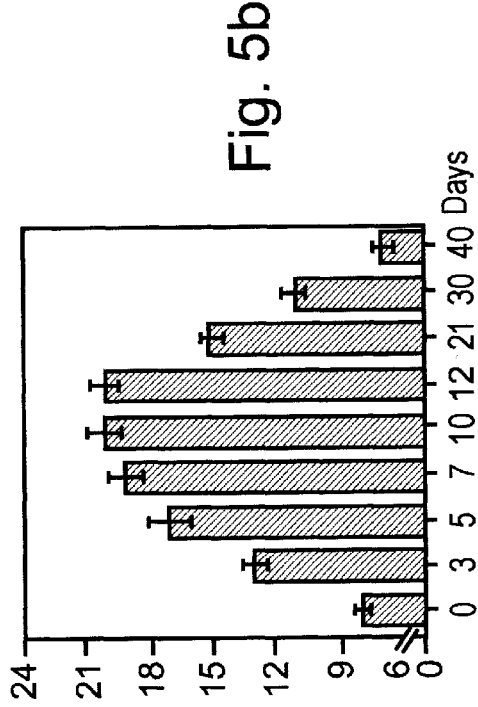
FIGS. 5a–d show the kinetics of antibody production in sera of EAE rats following C-C chemokine naked DNA vaccination. Rats were immunized weekly (three repeated immunizations) with the cloned PCR products of various C-C chemokines ligated into a pcDNA3 eukaryotic expression vector as described under FIG. 2a. Two weeks after the last immunization all rats were immunized with p68–86/CFA to induce active EAE. At different time points (0, 3, 5, 7, 10, 12, 21, 30 and 40 days after EAE induction) generation of anti-self antibody titer was determined as described under FIGS. 4a–d. Results are shown as mean $\log_2$ of four different samples±SE.
Figure 5B:
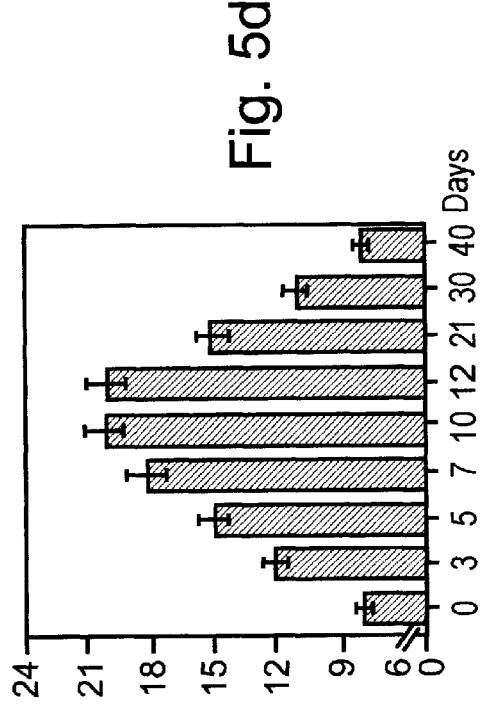
Figure 5C:
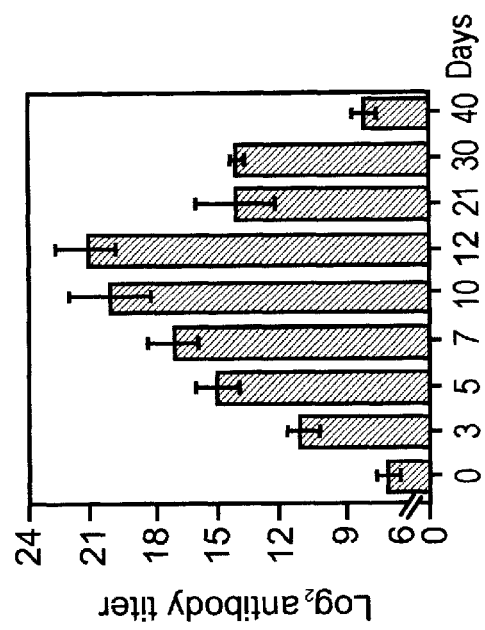
Figure 5D:
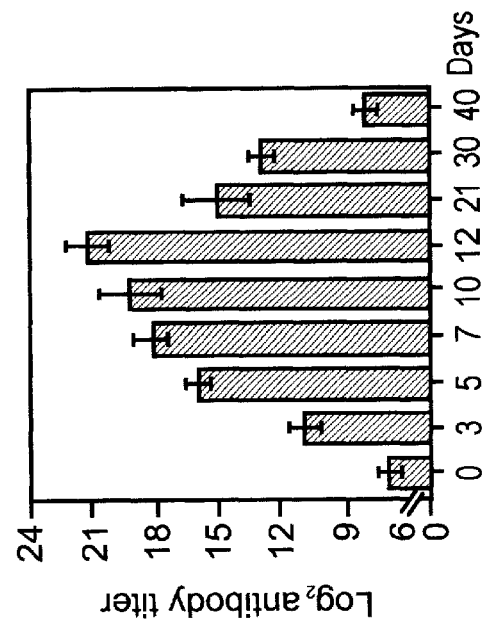
Figure 6A:
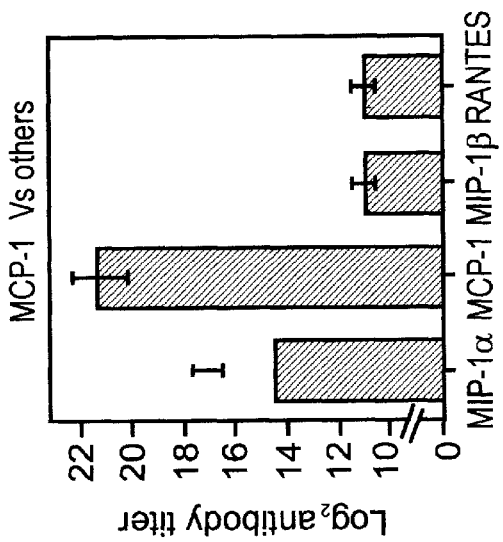
FIGS. 6a–d show vaccination with MCP-1 DNA elicited a significant cross-reactive immune response to MIP-1α. Twelve days after active induction of disease, sera of rats from the second experiment that were immunized with various C-C chemokine DNA vaccines and then challenged with p68–86/CFA (FIGS. 2b and 4a–d) were tested for the development of a cross reactive antibody titer between each of the four C-C chemokines: MIP1α (FIG. 6a) MCP-1 (FIG. 6b), MIP-1β (FIG. 6c), and RANTES (FIG. 6d). Results are shown as mean $\log_2$ of four different samples±SE.
Figure 6B:
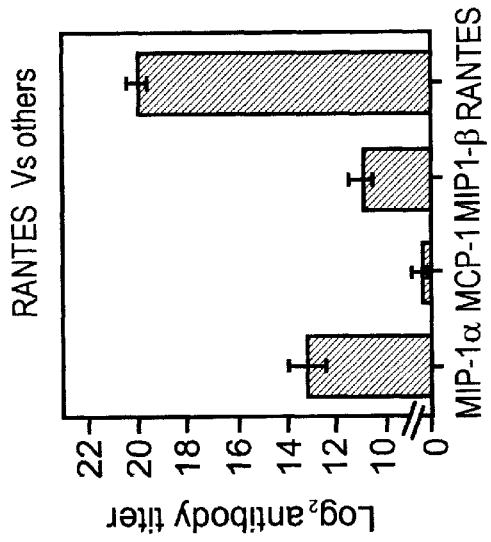
Figure 6C:
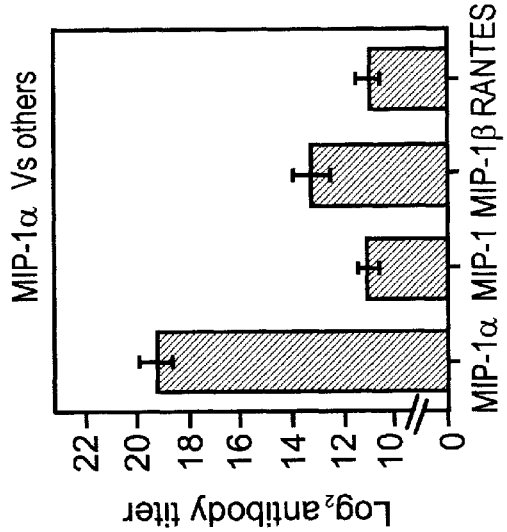
Figure 6D:
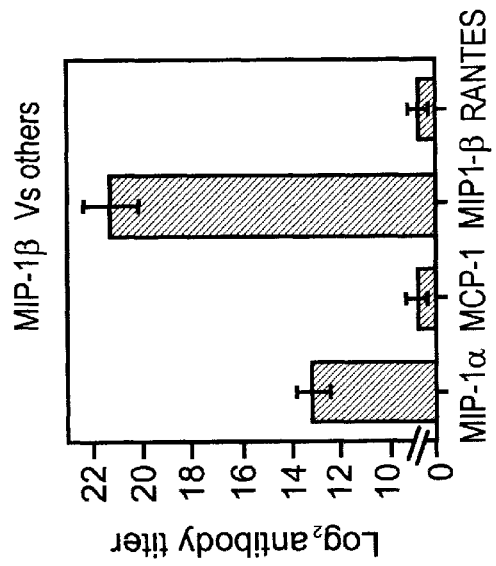

Prevention of RAE using C-C chemokine naked DNA vaccines: Cloned PCR products of each C-C chemokine, obtained as described above, were ligated into a pcDNA3 eukaryotic expression vector and used as constructs for naked DNA vaccination (FIGS. 2a–b). In a first experiment (FIG. 2a) rats were subjected to three weakly injections of each construct. Control rats were either injected with the pcDNA3 vector alone, or with PBS. Two weeks after the last immunization all rats were immunized with p68–86/CFA to induce active EAE. All control (PBS immunized) and pcDNA3 vaccinated rats developed active disease that persisted for 5–6 days (FIG. 2a, 6/6 in each group with a maximum clinical score 2.33±0.1 in control and 2±0.26 in pcDNA3 immunized rats). In contrast, rats injected with either MIP-1α or MCP-1 DNA naked DNA vaccines were resistant to EAE (incidence of 0/6 for MIP-1α and ⅙ for MCP-1 vaccinated rats with a maximum clinical score of 0 and 0.33±0.34, respectively, $p<0.001$ for each treatment compared with either control or pcDNA3 treatments). Thus, the subsequent in vivo immune response to MIP-1α or MCP-1 DNA vaccines prevented EAE. In contrast, administration of the MIP-1β naked DNA significantly aggravated active EAE (FIG. 2a, 6/6 in each group maximum clinical score 3.2±0.17 compared with 2.33±0.1 in control and 2±0.26 in pcDNA3 immunized rats, $p<0.033$ and 0.028 respectively).

MIP-1α, MCP-1 and MIP-1β mRNA transcription in EAE brains peaked at the onset of disease and declined during its remission, whereas RANTES transcription increased in EAE brains only following recovery (FIGS. 1a–d). Thus, intervention in EAE development by C-C chemokine DNA vaccines is effective provided that the related chemokine is highly transcribed at the site of inflammation at the onset of disease.

In a subsequent, second, experiment each of the above constructs, as well as pcDNA3 alone, were administered five rather than three times (FIG. 2b). As with the first experiment, MIP-1α and MCP-1 naked DNA vaccines effectively prevented the development of active EAE (incidence of ⅙ for each treatment with a maximum clinical score of 0.17±0.17, compared with 6/6 in either control and pcDNA treated rats, $p<0.001$ for each comparison), MIP-1β vaccine significantly aggravated the disease (FIG. 2b, 6/6 in each group maximum clinical score 3±0 compared with 2±0 in control and 1.33±0.21 in pcDNA3 immunized rats, $p<0.001$ for each comparison) and RANTES naked DNA vaccination did not exhibit any notable effect on disease manifestation. Five consecutive immunizations of pcDNA3 did, however, notably affect disease severity (maximum score in control rats 2±0 compared with 1.33±0.21 in pcDNA treated rats, $p<0.007$). It is possible that numerous subsequent immunizations of an eukaryotic vector with a viral promoter may affect cytokine production by T cells, as has recently been suggested (39).

When active EAE attained its maximal severity (day 12, FIG. 2b) spinal cord samples of representative animals from each group (second experiment) were evaluated histologically (Table 1, FIGS. 3a–g). While control EAE rats and rats previously immunized with pcDNA3 all displayed perivaseular legions with pdfcnqhymal mononuclear cell infiltration (FIGS. 3b–c, and Table 1, b and c, mean histological score 2.2±0.2 and 1.8±0.2, respectively) rats previously immunized with MIP-1α or MCP-1 naked DNA vaccines were either free of mononuclear cell infiltration, or exhibited minimal parenchymal infiltration (FIGS. 3d–e, and Table 1, d and e, compared with FIGS. 3b–c, and Table 1, b and c, mean histological score 0.2±0.2 and 0.4±0.24 compared with 1.8±0.2 and 2.2±0.2, $p<0.001$). In contrast, rats that were immunized with MIP-1β naked DNA vaccines manifested an extensive parunchymal mononuclear cell infiltration (FIG. 3f and Table 1, f, mean histological score 3±0). Thus, inhibition or exacerbaton of disease by various naked DNA vaccines could each be demonstrated histologically.

TABLE 1

MIP1-α and MCP-1 naked DNA vaccines decreases CNS mononuclear cell infiltration

| | Treatment[1] | EAE | Mean Score[2] | Histological |
|---|---|---|---|---|
| a | — | – | 0 ± 0 | |
| b | — | + | 2.2 ± 0.3 | |
| c | pcDNA3 alone | + | 1.8 ± 0.2 | |
| d | pcDNA3/MCP-1 | + | 0.2 ± 0.2* | |
| e | pcDNA3/MIP-1α | + | 0.4 ± 0.24* | |
| f | pcDNA3/MIP-1β | + | 3 ± 0** | |
| g | pcDNA3/RANTES | + | 1.8 ± 0.2 | |

[1]Rats were treated as described in legend to FIG. 2b.
[2]When active EAE attained its maximal clinical severity (day 12, second experiment, FIG. 2b), samples from the lower thoracic and lumbar regions of the spinal cord were histologically evaluated. Histological scores were determined using an 0 to 3 scale as described in the methods. The mean clinical score ± SE were calculated from 6 sections per spinal cord of 2 representative rats from each group.
*$p < 0.01$ for D and E compared with either B or C;
**$p < 0.001$ for f compared with either b or c.

Natural autoimmunity to C-C chemokines in EAE is augmented with naked DNA vaccination: The development of anti-self protective immunity in DNA vaccinated rats was evaluated. When active EAE attained its maximal severity (day 12, FIG. 2b), blood samples of all animals that were sacrificed for histological evaluation (second experiment, Table 1, FIGS. 3a–g) were analyzed for the production of antibodies against gene products of each vaccinated DNA (FIGS. 4a–d), for the kinetics of antibody production along the course of active disease (FIGS. 5a–d), and for the possible development of cross-reactive immunity between various chemokines (FIGS. 6a–d).

Rats, without DNA vaccination with developing EAE display a notable anti-self antibody titer to various C-C chemokines (to MCP-1, FIG. 4a, 12.25±0.55 Vs. 7±0.47; to MIP-1α, FIG. 4b, 11±0.47 Vs. 8.25±0.55 to MIP-1β FIG. 4c 11±0.47 Vs. 7±0.47; to RANTES, FIG. 4d 11.25±0.55 Vs. 7±0.47) which is, however, not sufficient to prevent the development of disease. Naked DNA vaccination, on the other hand, significantly augmented this antibody titer (FIGS. 4a–d, 14.5±0.33, 14.75±0.55, 16.25±0.72 and 17±0.66 in rats immunized with MCP-1, MIP-1α, MIP-1β or RANTES constructs Vs. 9±0.47, 8.5±0.33, 8.75±0.29 and 7±0.47 in rats immunized with pcDNA alone, p<0.05 for each reciprocal comparison, and vs. 7±0.47, 8.25±0.55, 7±0.47 and 7±0.47 in naive rats, p<0.05 for each reciprocal comparison, no significant difference was identified between rats immunized with pcDNA alone and naive controls). Nevertheless, the antibody titer in rats immunized with each C-C chemokine DNA except RANTES markedly increased following induction of active EAE, but not following an immunization with CFA without p68–86 (FIGS. 4a–d, 21.25±0.98 19.25±0.73, 21.25±0.99 and 20±0.47 in rats immunized with MCP-1, MIP-1α, MIP-1β or RANTES constructs and then with p68–86/CFA Vs. 14.75±0.55, 13.75±0.72, 15.25±0.55 and 17.5±1.1 in rats immunized with MCP-1, MIP-1α, MIP-1β or RANTES constructs and then with CFA, p<0.05, for each reciprocal comparison, except for the last one, 0.05 <p<0.1).

Thus, naked DNA vaccines may serve as a powerfill technique to generate protective immunity against autologous cytokines and provides a tool by which the immune system is encouraged to elicit anti-self protective immunity to restrain its own harmful reactivity only when such a response is needed.

Sera form each of the above groups, immunized with various DNA vaccines and then with p68–86/CFA, were analyzed for a possible development of cross reactive antibody titer (FIGS. 6a–d). Sera from MIP-1α, MIP-1β and RANTES DNA vaccinated rats manifested a highly specific titer against homologous antigen (p<0.05 for the compression of each titer to any of the other 3 chemokines). MCP-1 vaccinated rats, however, exhibited a significant cross reactive antibody titer against MIP-1α (FIG. 6b; 21.25±0.99 to self, 1740.66 to MIP-1αand 11±0.47 to either MIP-1β or RANTES; p<0.005 for the comparison of anti- MIP-1αto anti-MIP-1β or RANTES, antibody titer, and for the comparison of anti- self to anti- MIP-1αantibody titer). Since both MCP-1 and MIP-1αnaked DNA vaccines are protective, it is possible that the protective immunity generated by anti- MCP-1 DNA vaccination may be mediated at least in part by reaction with MIP-1α.

Since DNA vaccination elicits both cellular and humoral responses against products of a given construct it is difficult to know which of these responses contributed more to the development of EAE resistance in MCP-1 and MIP-1α DNA vaccinated rats. To evaluate the possible contribution of anti-self antibodies to the development of EAE resistance twelve days after active induction of EAE, when production of anti-self antibodies in naked DNA vaccinated rats attained at its maximal titer (FIGS. 5a–d), antibodies were purified (IgG fraction, protein G purification) and evaluated for their competence to inhibit the migration of oil-induced peritoneal macrophages in a Boyden chemotaxis chamber assay, as previously described (37). MCP-1 and MIP-1α specific antibodies produced in MCP-1 naked DNA vaccinated rats significantly blocked MCP-1 and MIP-1αinduced chemotaxis (Table 2, 70±7 and 88±12 Vs. 185±15, p<0.001 for each comparison), whereas MIP-1αspecific antibodies generated in MIP-1α naked DNA vaccinated rats effectively blocked MIP-1αinduced chemotaxis (63±4 Vs. 155±15, p<.001), and to a much lesser extent MCP-1 induced chemotaxis (144±11 Vs. 185±15, p<0.05, Table 2).

Thus, MCP-1 and MIP-1α chemokine specific antibodies generated in naked DNA vaccinated rats are neutralizing antibodies.

Figure 7:
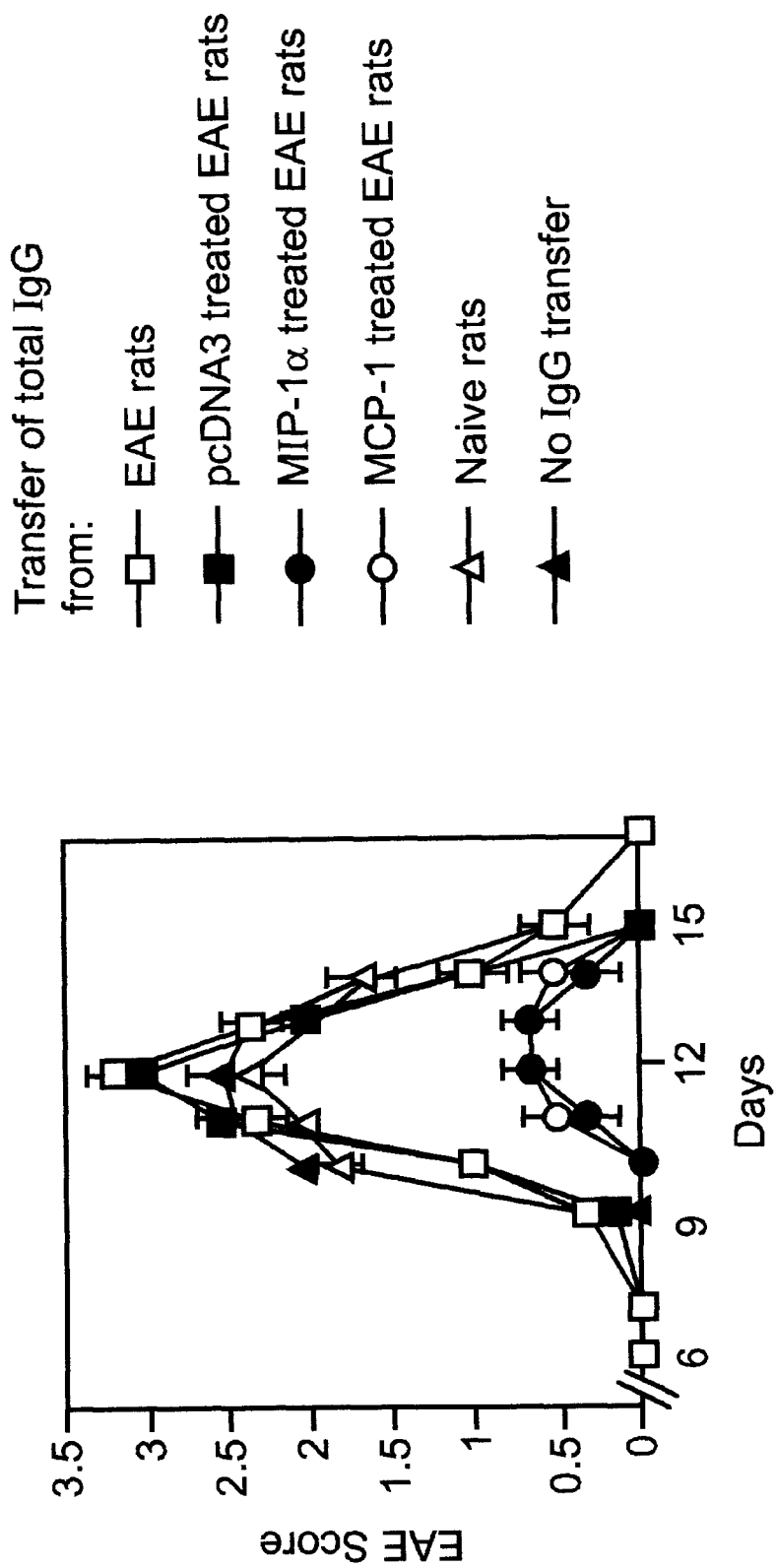
FIG. 7 show anti chemokine antibodies produced by DNA vaccination provide subsequent protection from severe EAE. Six groups of six rats were immunized with p68–86/CPA to develop active EAE. Four days before the onset of disease, rats were daily challenged (intravenously, days 6–13) with 100 μg of each of neutralizing antibodies (IgG fraction, protein G purification) purified from sera of rats that were previously vaccinated with various naked DNA vaccines, and were then subjected to active induction of EAE as described under FIG. 2a. Purified IgG fraction from rats that were, or were not, vaccinated with pcDNA3 and then subjected to active induction of disease, as well as sera from control rats that were, or were not, subjected to active induction of EAE were all used as controls. EAE was monitored daily by an observer blind to the treatment protocol. Results are shown as mean clinical score of six rats in each group ±SE.

These antibodies were then evaluated for their competence to provide subsequent protection from severe EAE (FIG. 7). Four days before the onset of active EAE, rats were daily challenged (days 6–13) with 100 μg of each of the above neutralizing antibodies, or with antibodies from rats that were vaccinated with pcDNA3 alone. Repeated administration of antibodies from MCP-1 and from MIP-1αDNA vaccinated rats provided substantial protection from disease progression (Mean maximal score of 0.66±0.2 in rats treated with purified antibodies from either MCP-1 or MIP-1α DNA vaccinated donors Vs. 3.16±0.2 and 3±0 in rats treated with purified antibodies from PBS or pcDNA3 treated rats, p<0.001 for each compression). In addition, elevated levels of MCP-1 and MIP-1α specific antibodies could be observed in spinal cord fluid (SCF) of EAE rats (day 12 of active EAE) that were previously subjected to MCP-1 or MIP-1αnaked DNA vaccines (log2 antibody titer of 27±3 and 18±2 to MCP-1 and MIP-1α in SCF of rats administered with MCP-1 naked DNA vaccine, and of 25±3 to MIP-1αin SCF of rats administered with MIP-1αnaked DNA vaccine, compared to 12±2 and 10±1 in SCF of rats treated with pcDNA3 or PBS, p<0.01 for each comparison. Rats administered with MIP-1α naked DNA vaccine did not generate a significant antibody titer to MCP-1 compared with rats administered with pcDNA3 or PBS). Thus, during the course of EAE neutralizing antibodies to MCP-1 and MIP-1α are generated in MCP-1 and MIP-1α DNA vaccinated rats and elevated levels of these antibodies can be identified at the site of inflammation in the CNS where they probably block disease progression.

TABLE 2

Antibodies from MIP-1α and MCP-1 naked DNA vaccinated rats block MIP-1α and MCP-1 induced chemotaxis in vitro

| | Purified antibodies (IgG) from | | | |
|---|---|---|---|---|
| Chemo-attractant | — Control EAE rats | MIP-1α[b] DNA vaccinated EAE rats | MCP1[b] DNA vaccinated EAE rats | pcDNA3[b] DNA vaccinated EAE rats |
| | | (cells/field ± SE) | | |
| Medium | 60 ± 6 | 66 ± 8 | 62 ± 4 | 57 ± 5 | 65 ± 6 |
| fMLP (10-7M) | 220 ± 14 | 213 ± 17 | 215 ± 17 | 211 ± 17 | 211 ± 19 |
| MIP-1α (200 ng/ml) | 155 ± 15 | 143 ± 10 | 63 ± 4* | 88 ± 12* | 144 ± 11 |
| MCP-1 (100 ng/ml) | 185 ± 15 | 179 ± 12 | 144 ± 11** | 70 ± 7* | 173 ± 10 |

Twelve days after active induction of EAE, when production of anti-self antibodies in naked DNA vaccinated rats attained at its maximal titer (FIGS. 5a–d), antibodies were purified (IgG fraction, protein G purification) and evaluated for their competence to inhibit the migration of oil-induced peritoneal macrophages in a Boyden chemotaxis chamber assay. fMLP (Sigma) was used as a positive control for Chemoattraction.
Result are shown as Mean of triplicates ± SE.
[b]Donor rats were treated as described in legend to FIG. 2a.
*P < 0.001;
**p < 0.05.

To further evaluate a possible association between disease manifestation and anti-self antibody production in naked DNA vaccinated rats the kinetics of anti-self antibody was carefully evaluated. Rats have been subjected to MCP-1, MIP-1αMIP-1β or RANTP naked DNA vaccines and then immunized with p68–86/CFA, as described under FIG. 2a. At different time points (0, 3, 5, 7, 10, 12, 21, 30 and 40 days after EAE induction) generation of anti-self antibody was determined (FIGS. 5a–d). Each antibody titer profoundly increased within five to seven days of MBP p68–86/CFA immunization (p<0.001 compared to the day 0). The increase, was simultaneous with the accelerated transcription of each chemokine mRNA at the site of inflammation (FIGS. 1a–d), suggesting that generation of each gene product at the site of inflammation elicits the production of anti-self antibodies. Each antibody titer peaked after the onset of disease (day 10–12) and returned to background within 40 days. Our data therefore clearly show that transcriptional up-regulaton of individual chemokines in the CNS can provide protection from disease progression.

Finally, the competence of C-C chemokine naked DNA vaccines to render long lasting protective immunity against EAE was evaluated. Rats were subjected to three weakly injections of C-C chemokine naked DNA vaccines as described above (first experiment, FIG. 2a). Two months after last vaccine was administered EAE was actively induced. Rats immunized with either MIP-1α or MCP-1 DNA vaccines were highly protected against EAE (incidence of 0/4 for each treatment, compared with 4/4 with a maximal score of 1.25±0.28 in either control and pcDNA treated rats, p<0.001 for each comparison). MIP-1β naked DNA vaccination, however, aggravated the disease (incidence 4/4 with a maximal score of 2.5±0.33, p<0.013 for each comparison).

Thus, MIP-1α and MCP-1 DNA vaccines generate long lasting protective immunity against autologous cytokines when such a response is needed.

Figure 8A:
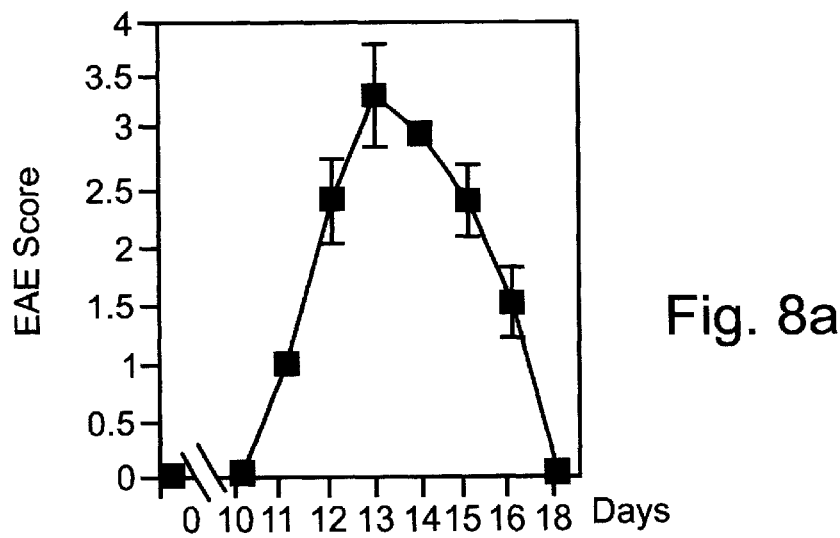
FIGS. 8a–c show the dynamics of mRNA transcription of TNF-α in the inflamed brain of transferred EAE rats. Rats were injected with $10^7$ L68–86 cells to develop transferred EAE (FIG. 8a). Before adoptive transfer of disease (day 0), and at various time points: before the onset of disease (day 3), at the day of onset (day 5), the peak (day 7), following recovery (day 10), and 10 days after recovery (day 20), mid-brain and brain stem samples from six different rats at each time point were examined. mRNA was isolated from each sample and subjected to RT-PCR analysis using specific oligonucleotide primers constructed to TNF-α (FIG. 8b). Each amplification was, calibrated to β-actin (FIG. 8c) and verified by Southern bolt analysis (FIGS. 8b–c).
Figure 8B:
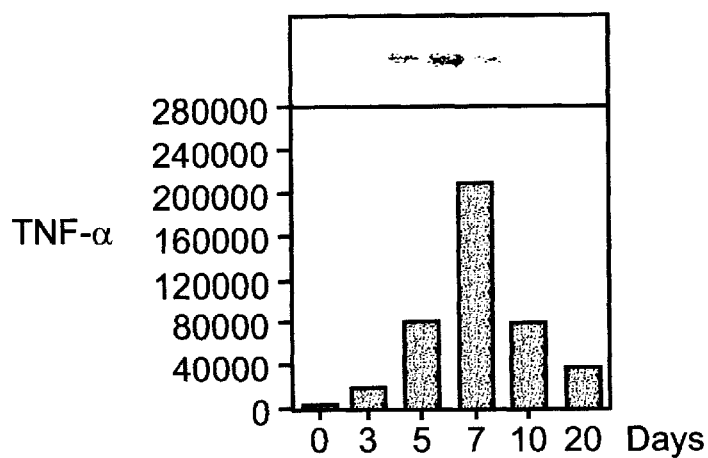

Dynamics of transcription TNF-α mRNAs in the inflamed brain: Rats injected with L68–86 developed transferred EAE that persisted for 5–6 days (FIG. 8a), Before adoptive transfer of disease (day 0), and at various time points: before the onset of disease (day 3), at the day of onset (day 5), the peak (day 7), following recovery (day 10), and 10 days after recovery (day 20) midbrain-brain stem samples were obtained from six different rats at each time point. From each sample mRNA was isolated and subjected to RT-PCR analysis using specific oligonucleotide primers. Each amplification was calibrated to β-actin and verified by Southern Blotting analysis. This enabled semi-quantitative analysis of the dynamics of mRNA transcription of TNF-α at the site of inflammation. FIG. 8b shows representative results from each time point of the experiment. Transcription of TNF-α in EAE brains was apparent at the onset of disease (day 5), peaked with at the fime when clinical disease attained it maximal severity (day 7), and gradually regressed following recovery. Notable transcription could, Nevertheless, still be observed even ten days after recovery (FIG. 8b).

Figure 8C:
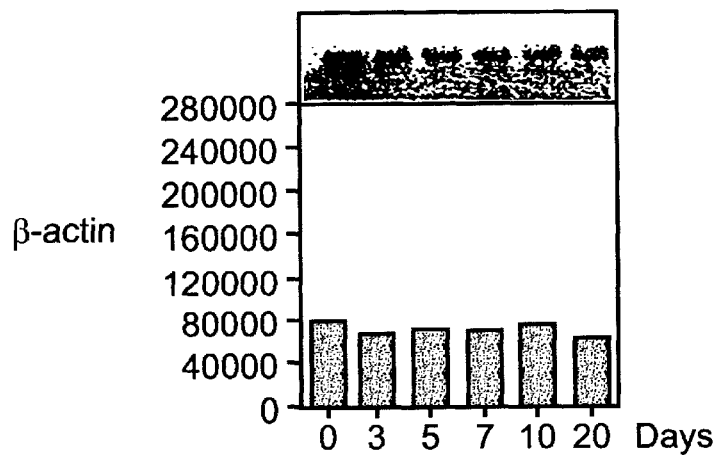
Figure 8D:
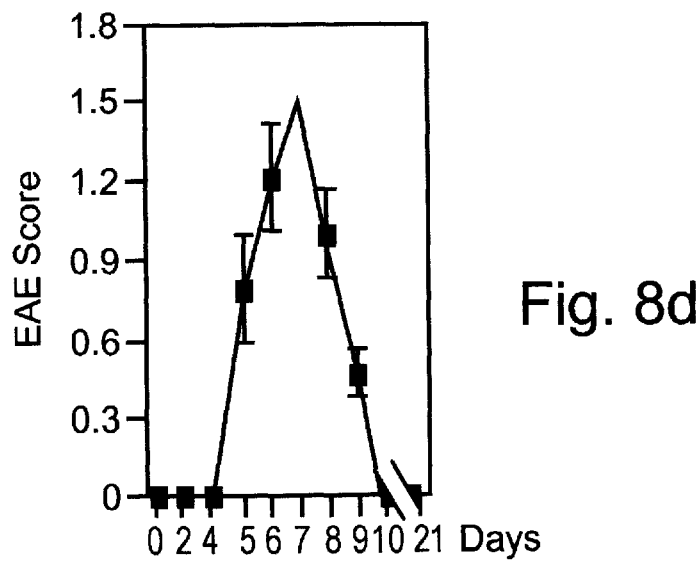
FIGS. 8d–f show the dynamics of mRNA transcription of TNF-α in the inflamed brain of active EAE rats. Rats were immunized with p68–86/CFA and developed active EAE (FIG. 8d). Before the induction of disease (day 0), and at various time points: before the onset of disease (day 8), at the peak (day 13) and 5 days after recovery (day 21) mid-brain and brain stem samples from six different rats at each time point, were obtained and subjected to RT-PCR as described with respect to FIGS. 8b–c. The results are shown in FIGS. 8e–f, respectively.
Figure 8E:
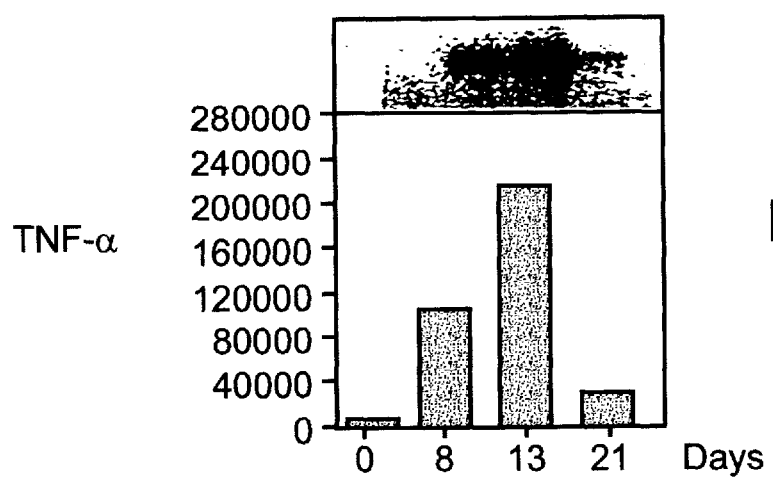
Figure 8F:
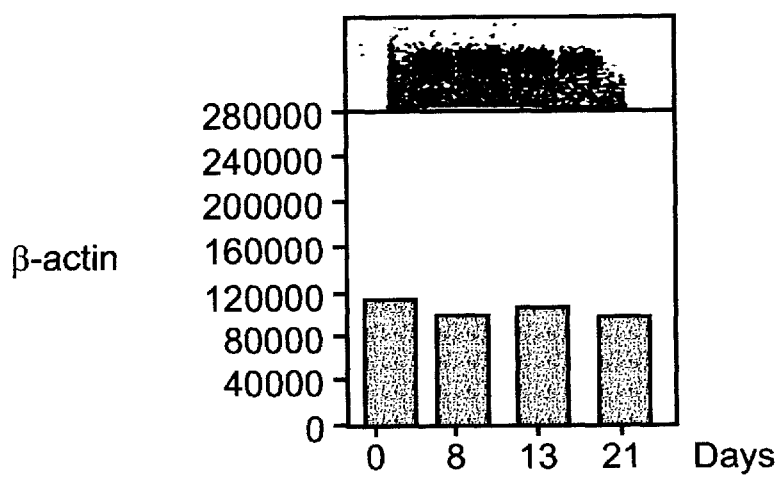
Figure 9:
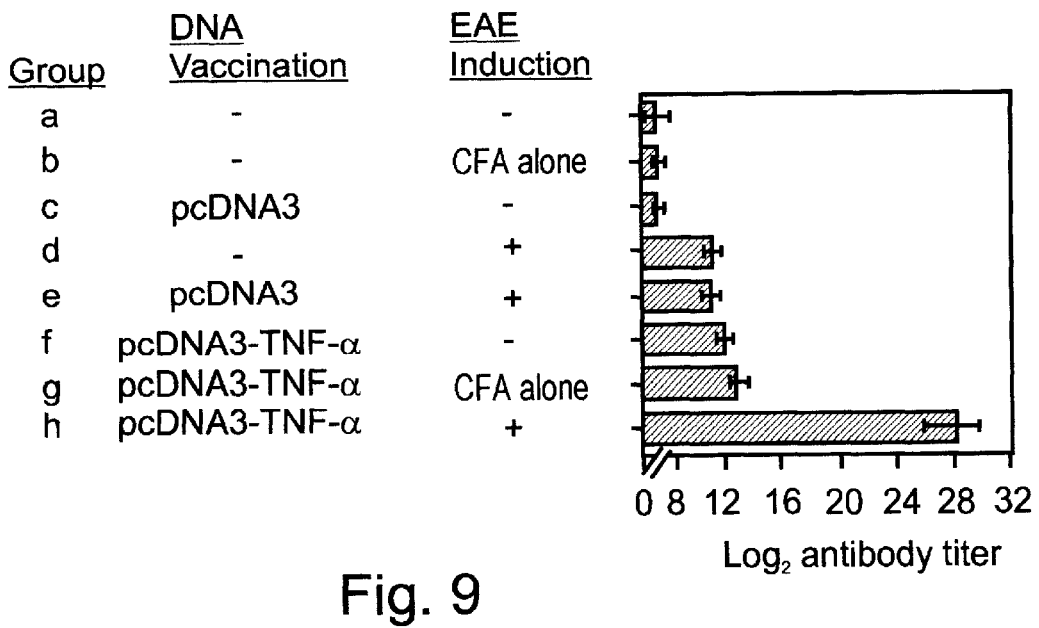
FIG. 9 shows that naked DNA encoding TNF-α augments transcriptionally regulated protective immunity. Twelve days after active induction of disease (with p68–86/CFA) sera of rats from experiment described in legend to FIG. 10, as well as sera from rats that received the same subsequent set of naked DNA vaccinations, but were finally challenged with the emulsion of PBS and CFA without p68–86, or from rats that received the same subsequent set of naked DNA vaccinations but were never challenged with p68–86/CA or CFA, were tested for antibody titer against TNF-α The assay conditions and data calculation of each test was done according to (14). Results are shown as mean log2 of four different samples±SE. Ab-antibody.

Rats with developing active disease (FIG. 8c) manifested similar mRNA transcription characteristics as those with developing transferred disease That is, an apparent transcription of mRNA encoding TNF-α at the CNS just before the onset of disease (day 8) with a substantial augmentation at the time when clinical disease attained it maximal severity (day 13), and marked regression following recovery (FIG. 8d).

Transcriptional induction of natural immune response to TNF-α in EAE rats: The development of anti-self immunity to TNF-α in EAE rats was evaluated. Just before active induction of disease (day 0) and when EAE attained its maximal severity (day 13, FIGS. 8a–b) blood samples were analyzed for the production of antibodies against self TNF-α. Rats, with developing EAE display a significantly increased TNF-α specific antibody titer as compared to rats immunized in hind foot pads with CFA alone (FIG. 9, d Vs. b, log2 antibody titer of 11±0.85 Vs. 7±0.66, respectively, p<0.05).

These results are remarkable since both groups exhibited an extensive local inflammatory process at the site of CFA immunization (hind foot pads), with a massive local transcription of TNF-α mRNA (data not shown). Nevertheless, only rats with developing EAE manifested an apparent transcription of mRNA encoding TNF-α at the CNS that substantially increased at the time when clinical disease attained it maximal severity (FIG. 8d). In contrast, rats immunized with CFA alone did not exhibit a notable transcription of mRNA encoding TNF-α at the CNS of all detected brain samples at various time points (0, 8, 13 and 21 days after CFA administration, data not shown). Thus, only the transcription of the inflammatory cytokine TNF-α at an privileged autoimmune site (CNS) enabled the triggering of an anti-self response against this pro-inflammatory cytokine. This response was, however, not sufficient to prevent the development of an autoimmune condition (6/6 sick rats, FIG. 10).

Prevention of EAE using TNF-α naked DNA vaccines: A PCR products of rat TNF-α, obtained as described above, was ligated into a pcDNA3 eukaryotic expression vector and used as construets for naked DNA vaccination (FIG. 10). Rats were subjected to three weakly injections of the above construct. Control rats were either injected with the pcDNA3 vector alone, or with PBS. Two months after the last immunization all rats were immunized with p68–86/CFA to induce active EAE. All control, i.e., PBS immunized and pcDNA3 vaccinated, rats developed active disease that persisted for 5–6 days (FIG. 10, 6/6 in each group with a maximum clinical score 3±0.28 in control, 2.83±0.18 in pcDNA3 immunized rats). In contrast, rats injected the TNF-α naked DNA vaccine were resistant to EAE (incidence of 2/6 with a maximum clinical score of 0.33±0.2, p<0.003 for each the treatment of TNF-α DNA naked DNA vaccine compared with either control or pcDNA3 treatments). Thus, the subsequent in vivo immune response to TNF-α naked DNA vaccine prevented EAE.

Figure 11:
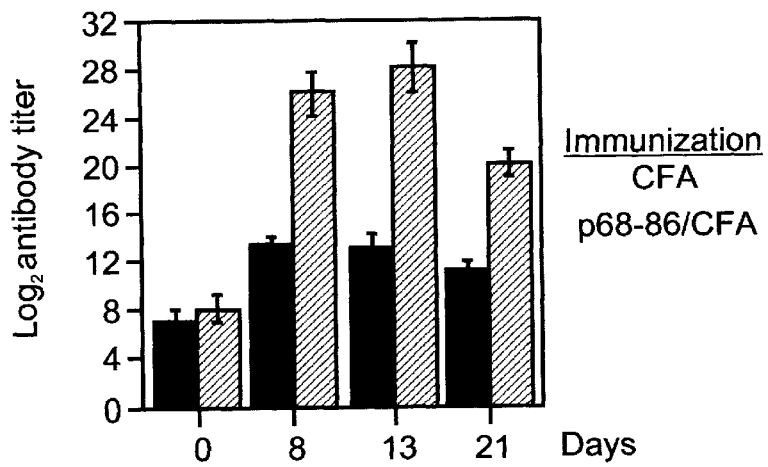
FIG. 11 shows the kinetics of antibody production in sera of EAE rats following TNF-α naked DNA vaccination. Rats were immunized weekly (three repeated immunizations) with the cloned PCR products of TNF-α ligated into a pcDNA3 eukaryotic expression vector. Two months after the last immunization all rats were immunized with either p68–86/CFA to induce active EAE, or with CFA alone. At different time points generation of anti-self antibody titer was determined as described under FIG. 9. Results are shown as mean log2 of four different samples±SE.

Naked DNA encoding TNF-α augments transcriptionally regulated protective immunity: The development of anti-self protective immunity in DNA vaccinated rats was evaluated. When active EAE attained its maximal severity (day 13) blood samples of representative rats from the experiment described under FIG. 10 were analyzed for the production of antibodies against TNF-α (FIG. 9, d–e and h), and for the kinetics of antibody production (FIG. 11). The notable anti-self antibody titer against TNF-α produced in EAE rats, without DNA vaccination (FIG. 9, d Vs. b, log2 antibody titer of 11±0.85 Vs. 7±0, respectively, p<0.05), which was not sufficient to prevent the development of disease, profoundly augmented in naked DNA vaccinated rats (FIG. 9, h Vs. d and e, log2 antibody titer of 28±1.88 in rats vaccinated with the TNF-α construct Vs. 8±0.8 in EAE rats vaccinated with pcDNA3 alone and 11±0.85 in control EAE rats, respectively, p<0.0001 for the comparison of h with either d or e).

At different time points: 0, 8, 13, and 21 days after active EAE induction, the kinetics of anti-self TNF-α antibody production was determined (FIG. 11). TNF-α specific antibody titer profoundly increased within eight days of MBP p68–86/CFA immunization (log2 antibody titer of 26±1.88 on day 8 Vs. 7±1 on day 0, p<0.001). The increase, was simultaneous with the accelerated transcription of TNF-α mRNA at the site of inflammation (FIGS. 8a–f). At this time a highly significant difference could be observed between the production of TNF-α specific antibody titer in TNF-α DNA vaccinated rats that were immunized with p68–86/CFA to those immunized with CFA alone (log2 antibody titer of 26±1.88 Vs. 13±0.6, p<0.001). Thus, administration of naked DNA encoding TNF-α augments transcriptionally regulated generation anti-self antibodies against a proinflammatory cytokine that are involved in the induction and progression of the autoimmulle condition.

Figure 12:
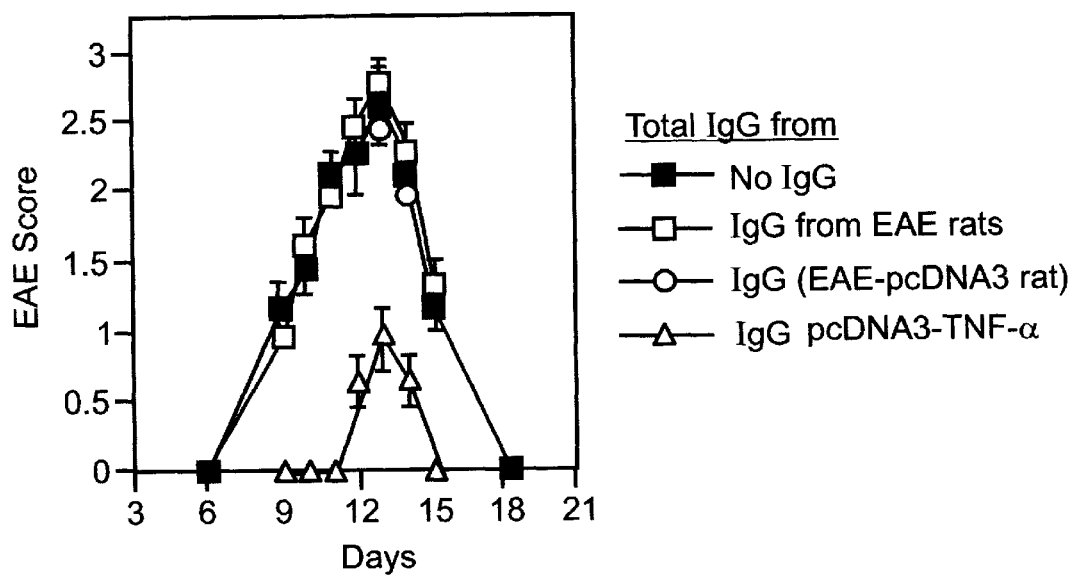
FIG. 12 shows that TNF-α specific antibodies produced by DNA vaccination provide subsequent protection from severe EAE. Six groups of six rats each were immunized with p68–86/CFA to develop active EAE. Four days before the onset of disease, rats were daily challenged (intravenously, days 6–13) with 100 μg of each of TNF-α specific neutralizing antibodies (IgG fraction, protein G purification) purified from sera of rats that were previously vaccinated with various naked DNA vaccines, and were then subjected to active induction of EAE as described under FIG. 10. Purified IgG fraction from rats that were, or were not vaccinated with pcDNA3 and then subjected to active induction of disease, as well as sera from control rats that were, or were not subjected to active induction of EAE were all used as controls. EAE was monitored daily by an observer blind to the treatment protocol. Results are shown as mean clinical score of six rats in each group±SE.

TNF-α specific anti-self antibodies from naked DNA vaccinated rats transfer EAE resistance: Since DNA vaccination elicits both cellular and humoral respongeg against products of a given construct it is difficult to know which of these responses contributed more to the development of EAE resistance in. TNF-α DNA vaccinated rats. To evaluate the possible contribution of anti-self antibodies to the development of EAE resistance twelve-thirteen days after active induction of EAE, when production of anti-self antibodies in naked DNA vaccinated rats attained at its maximal titer (FIG. 11), antibodies were purified (IgG fraction, protein G purification) and evaluated for their competence to provide subsequent protection from severe EAE (FIG. 12). Four days before the onset of active EAE, rats were daily challenged (days 6–13) with 100 μg of each of antibodies, or with antibodies from rats that were vaccinated with either pcDNA3-TNP-α construct, or with pcDNA3 alone. Repeated administration of antibodies from TNF-α DNA vaccinated rats provided substantial protection from disease progression (Mean maximal score of 1±0.2 in rats treated with purified antibodies from TNF-α DNA vaccinated donorg VS. 2.66±03 and 2.83±0816 in rats treated with purified antibodies from PBS or pcDNA3 treated rats, respectively, p<0.001 for each compression).

Taken together these results show that administration of naked DNA encoding TNF-α augments transcriptionally regulated generation anti-self antibodies capable of blocking the development of an experimental autoimmune disease of the CNS and thus providing a tool by which the immune system is encouraged to elicit anti-self protective immunity to restrain its own harmful reactivity only when such a response is needed.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

LIST OF REFERENCES CITED

1. Alvord, E. C. J., M. W. Kies, and A. J. Suclding. 1984. Experimental Allergic Encephalomylitis: A useful Model for Multiple Sclerosis. In *Progress in clinical and biological research.*, vol. 146. E. C. J. Alvord, M. W. Kies, and A. J. Suckling, eds. Allen R. Liss, New York, p. 1–537.
2. MacFarlin, D., and H. MacFarland. 1983. Multiple Sclerosis. *N. Eng.J.Med* 307.1183–1188.
3. Karin, N., F. Szafer, D. Mitchell, D. P. Gold, and L. Steinman. 1993. Selective and nonselective stages in homing of T lymphocytes to the central nervous system during experimental allergic encephalomyelitis. *J Immunol* 150:4116–24.
4. Yednock, T. A., C. Cannon, L. C. Fritz, M. F. Sanchez, L. Steinman, and N. Karin. 1992. Prevention of experimental autoimmune encephalomyelitis by antibodies against alpha 4 beta 1 integrin. *Nature* 356.63–6.
5. Brocke, S., K. Gijbels, M. Allegretta, I. Ferber, C. Piercy, T. Blankenstein, R. Martin, U. Utz, N. Karin, D, Mitchell, and at al. 1996. Treatment of experimental encephalomyelitis with a peptide analog of myelin basic protein. *Nature* 3 79:343–6.
6. Schmied, M., H. Breitschopf, R. Gold, H. Zischler, G. Rothe, H. Wekerle, and H. Lassmann. 1993. Apoptosis of T lymphocytes in experimental autoimmune encephalomyelitis; Evidence for programmed cell death as a mechanism to control inflammation in the brain. *Americam Journal of Pathology* 143:446–451.
7. Karin, N., J. D. Mitchell, S. Brocke, N. Ling, and L. Steinman. 1994. Reversal of experimental autoimmune encephalomyelitis by as soluble peptide variant of a myclin basic protein epitope: T cell receptor antagonism and reduction of IFN-g and TNF-α production. *J Exp. Med.* 160;2227–2237.
8. Xiang, Z., and H. C. Ertl. 1995. Manipulation of the immune response to a plasmid-encoded viral antigen by coinoculation with plasmids expressing cytokines. *Immunity* 2:129–35.
9. Irvine, K. R., J. B. Rao, S. A. Rosenberg, and N. P. Restifo. 1996. Cytokine enhancement of DNA immunization leads to effective treatment of established pulmonary metastases. *Journal of Immunology* 156:238–45.
10. Ulmer, J. B., J. C. Sadoff, and M. A. Liu. 1996. DNA vaccines. *Current opinion in immunology* 8:531–536.
11. Barry, M. A., W. C. Lai, and S. A. Johnston. 1995. Protection against mycoplasma infection using expression-library immunization. *Nature* 377:632–5.
12. Sedegah, M., R. Hedstrom, P. Hobart, and S. L. Hoffman. 1994. Protection against malaria by immunization with plasmid DNA encoding circumsporozoite protein. *Proc Natl Acad Sci U S A* 91:9866–70.
13. Tang, D. C., M. DeVit, and 9. A. Johnston. 1992, Genetic immunization is a simple method for eliciting an immune response. *Nature* 356:152–4.
14. Ulmer, J. B., J. J. Donnelly, S. E. Parker, G. H. Rhodes, P. L. Felgner, V. J. Dwarki, S. H. Gromkowski, R. R. Deck, C. M. DeWitt, A. Friedman, and at al. 1993. Heterologous protection against influenza by injection of DNA encoding a viral protein [see comments]. *Science* 259:1745–9.
15. Sato, Y., M. Rordan, H. Tighe, D, Lee, M. Corr, M. Nguyen, G. J. Silverman, M. Lotz, D. A. Carson, and E. Raz. 1996. Immunostimulatory DNA sequences necessary for effective intradermal gene immunization. *Science.*
16. Singh, R. R., V. Kumar, F. M. Ebling, S. Southwood, A. Sette, E. E. Sercarz, and B. H. Hahn. 1995. T cell determinants from autoantibodies to DNA can upregulate autoimmunity in murine systemic lupus erythematosus. *Journal of Experimental Medicine* 181:2017–27.
17. Waisman, A., P. J. Ruiz, D. L. Hirschberg, A. Gelman, J. R. Oksenberg, S. Brocke, F. Mor, I. R. Cohen, and L. Steinman. 1996. Suppressive vaccination with DNA encoding a variable region gene of the T-cell receptor prevents autoimmune encephalomyelitis and activates Th2 immunity. *Nature Medicine* 2:899–905.
18. Bazan, J. F., K. B. Bacon, G. Hardiman, W. Wang, K. Soo, D. Rossi, D. R. Greaves, A. Zlotnik, and T. J. Schall. 1997. A new class of membrane-bound chemokine with a CX3C motif *Nature* 385:640–4.
19. Pan, Y., C. Lloyd, H. Zhou, S. Dolich, J. Deeds, J. A. Gonzalo, J. Vath, M. Gosselin, J. Ma, B. Dussault, E. Woolf, G. Alperin, J. Culpepper, J. C. Gutierrez-Ramos, and D. Gearing. 1997. Neurotactin, a membrane-anchored chemokine upregulated in brain inflammation. *Nature* 387.611–7.
20. Ben-Baruch, A., D. F. Michiel, and J. J. Oppenheim. 1995. Signals and receptors involved in recruitment of inflammatory cells. *J Biol Chem* 270:11703–6.

21. Ponath,, P. D., S. Qin, D. J. Ringler, I. Clark-Lewis, J. Wang, N. Kassam, H. Smith, X. Shi, J. A. Gonzalo, W. Newman, J. C. Gutierrez-Ramos, and C. R. Mackay. 1996. Cloning of the human eosinophil chemoattractant, eotaxin. Expression, receptor binding, and functional properties suggest a mechanism for the selective recruitment of eosinophils. *J Clin Invest* 97:604–12.

22. Carf, M. W., R. Alon, and T. A. Springer. 1996. The C-C chemokine MCP-1 differentially modulates the avidity of beta 1 and beta 2 integrins on T lymphocytes. *Immunity* 4:179–87.

23. Lloyd, A. R., J. J. Oppenheim, D. J. Kelvin, and D. D. Taub. 1996. Chemokines regulate T cell adherence to recombinant adhesion molecules and extracellular matrix proteins. *Journal of Immunology* 156:932–8.

24. Bacon, K. B., L. Flores-Romo, J. P. Aubry, T. N. Wells, and C. A. Power. 1994. Interleukin-8 and RANTES induce the adhesion of the human basophilic cell line KU-812 to human endothelial cell monolayers. *Immunology* 82:473–81.

25. Brown, Z., M. E. Gerritsen, W. W. Carley, R. M. Strieter, S. L. Kunkel, and J. Westwick. 1994. Chemokine gene expression and secretion by cytokine-activated human microvascular endothelial cells. Differential regulation of monocyte chemoattractant protein-1 and interleukin-8 in response to interferon-gamma. *American Journal of Pathology* 145:913–21.

26. Carlos, T. M., and J. M. Harlan. 1994. Leukocyte-endothelial adhesion molecules. *Blood* 84:2068–101.

27. Jutila, M. A. 1994. Role of changes in the vascular endothelium in chronic inflammation. *Clinical Transplantation* 8:304–7.

28. Kim, J. S., S. C. Gautain, M. Chopp, C. Zaloga, M. L. Jones, P. A. Ward, and K. M. Welch. 1995. Expression of monocyte chemoattractant protein-1 and macrophage inflammatory protein-1 after focal cerebral ischemia in the rat. *Journal of Neuroimmunology* 56:127–34.

29. Lukacs, N. W., R. M. Strieter, V. Elner, H. L. Evanoff, M. D. Buraick, and S. L. Kunkel. 1995. Production of chemokines, interleukin-8 and monocyte chemoattractant protein-i, during monocyte: endothelial cell interactions. *Blood* 86;2767–73.

30. Schall, T. J., K. Bacon, R. D. Camp, J. W. Kaspari, and D. V. Goeddel. 1993. Human macrophage inflammatory protein alpha (MIP-1 alpha) and MIP-1 beta chemokines attract distinct populations of lymphocytes. *Journal of Experimental Medicine* 177:1821–6.

31. Vaddi, K., and R. C. Newton. 1994. Regulation of molocyte integrin expression by beta-family chemokines. *Journal of Immunology* 153:4721–32.

32. Yu, X., and D. T. Graves. 1995. Fibroblasts, mononuclear phagocytes, and endothelial cells express monocyte chemoattractant protein-1 (MCP-1) in inflamed human gingiva. *Journal of Periodontology* 6;80–8.

33. Karpus, W. J., N. W. Lukacs, B. L. McRae, R. M. Strieter, S. L. Kunkel, and S, D. Miller. 1995. An important role for the chemokine macrophage inflammatory protein-1 alpha in the pathogenesis of the T Cell-mediated autoimmune disease, experimental autoimmune encephalomyelitis. *J Immunol* 155:5003–10.

34. Gong, J. H., L. G. Ratkay, J. D. Waterfield, and I. Clark-Lewis. 1997. An antagonist of monocyte chemoattractant protein 1 (MCP-1) inhibits artitis in the MRL-1pr mouse model. *J Exp Med* 186:131–7.

35. Berman, J. W., M. P. Guida, J. Warren, J. Amat, and C. F. Brosnan. 1996. Localization of monocyte chemoattactant peptide-1 expression in the central nervous system in experimental autoimmune encephalomyelitis and trauma in the rat. *J Immunol.* 156:3017–3023, 36. Ben-Nun, A., H. Wekerle, and I. R. Cohen. 1981. The rapid isolation of clonable antigen-specific T lymphocyte lines capable of mediating autoimmune encephalomyelitis. *Eur Immunol* 11:195–9.

37. Lanir, N., P. S. Ciano, L. Van de Water, J. McDonagh, A. M. Dvorak, and H. F. Dvorak. 1988. Macrophage migration in fibrin gel matrices. II. Effects of clotting factor XIII, fibronectin, and glycosaminoglycan content on cell migration. *J Immunol* 140:2340–9.

38. Luo, Y., J. Lanifig, S, Devi, J. Mak, T. J. Schall, and M. E. Dorf. 1994. Biologic activities of the murine beta-chemokine TCA3. *J Immunol* 153:4616–24.

39. Raz, E., H. Tighe, Y. Sato, M. Corr, J. A. Dudler, M. Roman, S. L. Swain, H. L. Spicgelberg, and D. A. Carson. 1996. Preferential induction of a Th1 immune response and inhibition of specific IgE antibody formation by plasmid DNA immunization. *Proc Natl Acad Sci USA* 93:5141–5.

40. Godiska, R., D. Chantry, G. N. Dietsch, and P. W. Gray. 1995. Chemokine expression in murine experimental allergic encephalomyelitis. *J Neuroimmunol* 58:167–76.

41. Kim, J. J., M. L. Bagarazzi, N. Trivedi, Y. Hu, K. Kazahaya, D. M. Wilson, R. Ciccarelli, M. A. Chattergoon, K. Dang, S. Mahalingam, A. A. Chalian, M. G. Agadjanyan, J. D. Boyer, P. Wang, and D. B. Weiner. 1997. Engineering of in vivo immune responses to DNA immunization via codelivery of costimulatory molecule genes. *Nat Biotechnol* 15:641–6.

42. Kim, J. J., V. Ayyavoo, M. L. Bagarazzi, M. A. Chattergoon, K. Dang, B. Wang, J. D. Boyer, and D. B. Weiner. 1997. In vivo engineering of a cellular immune response by coadministration of IL-12 expression vector with a DNA immunogen. *J Immunol* 158:816–26.

43. Fu, T. M., J. B. Ulmer, M. J. Caulfield, R. R. Deck, A. Friedman, S. Wang, X. Liu, J. J. Donnelly, and M. A. Liu. 1997. Primng of cytotoxic T lymphocytes by DNA vaccines: requirement for professional antigen presenting cells and evidence for antigen transfer from myocytes. *Mol Med* 3:362–71.

44. Carr, M. W., S. J. Roth, E. Luther, S. S. Rose, and T. A. Springer. 1994. Monocyte chemoattractant protein 1 acts as a T-lymphocyte chemoattractant. *Proc Natl Acad Sci USA* 91:3652–6.

45. Lloyd, C. M., A. W. Minto, M. E. Dorf, A. Proudfoot, T. N. Wells, D. J. Salant, and J. C. Gutierrez-Ramos. 1997. RANTES and monocyte chemoattractamt protein-1 (MCP-1) play an important role in the inflammatory phase of crescentic nephritis, but only MCP-1 is involved in crescent formation and interstitial fibrosis. *J Exp Med* 185:1371–80.

46. Uguccioni, M., M. D'Apuzzo, M. Loetscher, B. Dewald, ano M. Baggiolini. 1995. Actions of the chemotactic cytokines MCP-1, MCP-2, MCP-3, RANTES, MIP-1 alpha and MIP-1 beta on human monocytes. *Eur J Immunol* 25:64–8.

47. del Pozo, M. A., P. Sanchez-Mateos, M. Nieto, and F. Sanchez-Madrid. 1995. Chemokines regulate cellular polarization and adhesion receptor redistribution during lymphocyte interaction with endothelium and extracellular matrix. Involvement of cAMP signaling pathway. *J Cell Biol* 131:495–508.

48. Lukacs, N. W., R. M. Strieter, V. M. Elner, H. L. Evanoff, M. Burdick, and S. L. Kunkel. 1994. Intercellular adhesion molecule-1 mediates the expression of monocyte-derived MIP-1 alpha during monocyte-endothelial cell interactions. *Blood* 83.1174–8.

49. Weber, C., R. Alon, B. Moser, and T. A. Springer. 1996. Sequential regulation of alpha 4 beta 1 and alpha 5 beta 1 integrin avidity by CC chemokines in monocytes: implications for transendothelial chemotaxis. *J Cell Biol* 134:1063–73.
50. Riethmuller, G., E. P. Rieber, S. Kiefersauer, J. Prinz, P. van der Lubbe, B. Meiser, F. Breedveld, J. Eisenburg, K. Kruger, K. Deusch, and at al. 1992. From antilymphocyte serum to therapeutic monoclonal antibodies: first experiences with a chimeric CD4 antibody in the treatment of autoimmune disease. *Immunol Rev* 129:81–104.
51. Green, L. L., M. C. Hardy, C. E. Maynard-Currie, H. Tsuda, D. M. Louie, M. J. Mendez, H. Abderrahim, M. Noguchi, D. H. Smith, Y. Zeng, and at al. 1994. Antigen-specific human monoclonal antibodies from mice engineered with human Ig heavy and light chain YACs. *Nat Genet* 7:13–21.
52. Glabinski, A. R., M. Tani, R. M. Strieter, V. K. Tuohy, and R. M. Ransohoff. 1997. Synchronous synthesis of alpha- and beta-chemokines by cells of diverse lineage in the central nervous system of mice with relapses of chronic experimental autoimmune encephalomyelitis. *Am J Pathol* 150:617–30.
53. Issazadeh, S., A. Ljungdahl, B. Hojeberg, M. Mustafa, and T. Olsson. 1995. Cytokine production in the central nervous system of Lewis rats with experimental autoimmune encephalomyelitis: dynamics of mRNA expression for interleukin-10, interleukin-12, cytolysin, tumor necrosis factor alpha and tumor necrosis factor beta. *J Neuroimmunol* 61:205–12.
54. Kennedy, M. K., D. S. Torrance, K. S. Picha, and K. M. Mohler. 1992. Analysis of cytokine mRNA expression in the central nervous system of mice with experimental autoimmune encephalomyelitis reveals that IL-10 mRNA expression correlates with recovery. *J Immunol* 149:2496–505.
55. Villarroya, H., Y. Marie, J. C. Ouallet, F. Le Sauyx, J. L. cholingerian, and N. Baumann. 1997. Expression of TNF alpha in central neurons of Lewis rat spinal cord after EAE induction. *J Neurosci Res* 49:592–9.
56. Liu, J., M. W. Marino, G. Wong, D. Grail, A. Dunn, J. Bettadapura, A. J. Slavin, L. Old, and C. C. Bernard. 1998. TNF is a potent anti-inflammatory cytokine in autoimmune-mediated demyelination. *Nature Medicine* 4:78–83.
57. Kuroda, Y., and Y. Shimamoto. 1991. Human tumor necrosis factor-alpha augments experimental allergic encephalomyelitis in rats. *J Neuroimmunol* 34:159–64.
58. Powell, M. B., D. Mitchell, J. Lederman, J. Buckmeier, S. S. Zamvil, M. Graham, N. H. Ruddle, and L. Steinman. 1990. Lymphotoxin and tumor necrosis factor-alpha production by myelin basic protein-specific T cell clones correlates with encephalitogenicity. *Int Immunol* 2:539–44.
59. Ruddle, N. H., C. M. Bergman, K. M. McGrath, E. G. Lingenheld, M. L. Grunnet, S. J. Padula, and R. B. Clark. 1990. An antibody to lymphotoxin and tumor necrosis factor prevents transfer of experimental allergic encephalomyelitis. *J Exp Med* 172:1193–200.
60. Selmaj, K., C. S. Raine, and A. H. Cross. 1991. Anti-tumor necrosis factor therapy abrogates autoimmune demyelination. *Ann Neurol* 30:694–700.
61. Thornhill, M. H., S. M. Wellicome, D. L. Mahiouz, J. S. Lanchbury, A. U. Kryan, and D. O. Haskard. 1991. Tumor necrosis factor combines with IL-4 or IFN-gamma to selectively enhance endothelial cell adhesiveness for T cells. The contribution of vascular cell adhesion molecule-1-dependent and -independent binding mechanisms. *J Immunol* 146:592–8,
62. Korner, H., F. A. Lemckert, G. Chaudri, S. Etteldorf, and J. D. Sedgwick. 1997. Tumor necrosis factor blockade in actively induced experimental autoimmune encephalomyelitis prevents clinical disease despite activated T cell infiltration to the central nervous system. *Eur J Immunol* 27:1973–81.
63. Komer, H., D. S. Riminton, D. H. Strickland, F. A. Lemckert, J. D. Pollard, and J. D. Sedgwick. 1997. Critical points of tumor necrosis factor action in central nervous system autoimmune inflammation defined by gene targeting. *J Exp Med* 186:1585–90.
64. Suen, W. E., C. M. Bergman, P. Hjelmstrom, and N. H. Ruddle. 1997. A critical role for lymphotoxin in experimental allergic encephalomyelitis. *J Exp Med* 186:1233–40.
65. Taupin, V., T. Renno, L. Bourbonniere, A. C. Peterson, M. Rodriguez, and T. Owens. 1997. Increased severity of experimental autoimmune encephalomyelitis, chronic macrophage/microglial reactivity, and demyelination in transgenic mice producing tumor necrosis factor-alpha in the central nervous system. *Eur J Immunol* 2 7:905–13.
66. Brenner, T., S. Brocke, F. Szafer, R. A. Sobel, J. F. Parkinson, D. He Perez, and L. Steinman. 1997. Inhibition of nitric oxide synthase for treatment of experimental autoimmune encephalomyelitis. *J Immunol* 158:2940–6.
67. Frei, K., H. P. Eugster, M. Bopst, C. S. Constaiitinescu, E. Lavi, and A. Fontana. 1997. Tumor necrosis factor alpha and lymphotoxin alpha are not required for induction of acute experimental autoimmune encephalomyelitis. *J Exp Med* 185:2177–82.
68. Pan, W., W. A. Banks, M. K. Kennedy, E. G. Gutierrez, and A. J. Kastin. 1996. Differential permeability of the BBB in acute EAE: enhanced transport of TNT-alpha. *Am J Physiol* 271:E636–42.
69. Becher, B., V. Dodelet, V. Fedorowicz, and J. P. Antel. 1996. Soluble tumor necrosis factor receptor inhibits interleukin 12 production by stimulated human adult microglial cells in vitro. *J Clin Invest* 98:1539–43.
70. Leonard, J. P., K. E. Waldburger, and S. J. Goldman. 1995. Prevention of experimental autoimmune encephalomyelitis by antibodies against interleukin 12. *J Exp Med* 181:381–6.
71. Selmaj, K., W. Papierz, A. Glabinski, and T. Kohno. 1995. Prevention of chronic relapsing experimental autoimmune encephalomyelitis by soluble tumor necrosis factor receptor I. *J Neuroimmunol* 56:135–41.
72. Pette, M., K. Fujita, B. Kitze, J. N. Whitaker, E. Albert, L. Kappos, and H. Wekerle. 1990. Myelin basic protein specific T lymphocyte lines from MS patients and healthy individuals. *Neurology* 40:1770–6.
73. Chen, Y., V. K. Kuchroo, J. Inobe, D. Hafler, and H. L. Weiner. 1994. Regulatory T-cell clones induced by oral tolerance: Suppression of autoimmune encephalomyelitis. *Science* 265:1237–1240.
74. Rapoport, M. J., A. Jaramillo, D. Zipris, A. Lazarus, D. V. Serreze, E. H. Leiter, P. Cyopick, J. S. Danska, and T. L. Delovitch. 1993. Interleukin-4 reverses T cell proliferative unresponsiveness and prevents the onset of diabetes in nonobese diabetic mice. *J Exp. Med.* 178:87–99.
75. Friedman, A., and H. L. Weiner. 1994. Induction of anergy or active suppression following oral tolerance is determined by antigen dosage. *Proc Natl Acad Sci USA* 91:6688–6692.
76. Khoury, S. J., W. W. Hancock, and H. L. Weiner. 1992. Oral tolerance to myelin basic protein and natural recovery from experimental autoimmune encephalomyelitis are associated with downregulation of inflammatory cytokines and differential upregulation of transforming growth factor beta, interleukin 4, and prostaglandin E expression in the brain. *J Exp Med* 176:1355–64.

77. Cash, E., A. Minty, P. Ferrara, D. Caput, D. Fradelizi, and 0. Rott. 1994. Macrophage-inactivating IL-13 suppresses experimental autoimmune encephalomyelitis in rats. *J Immunol* 153:4258–67.

78. Saoudi, A., J. Kuhn, K. Huygen, K. Y. de, T. Velu, M. Goldman, P. Druet, and B. Bellon. 1993. TH2 activated cells prevent experimental autoimmune uveoretinitis, a TH1-dependent autoimmune disease. *Eur Jimmunol* 23:3096–103.

79. Liblau, R. S., S. M. Singer, and H. O. McDevitt. 1994. Th1 and Th2 CD4+0 T-Cells in the pathogenesis of organ-specific autoimmune diseases. Immunol. Today in press.

80. Racke, M. K., J. S. Dhib, B. Cannella, P. S. Albert, C. S. Raine, and D. E. McFarlin. 1991. Prevention and treatment of chronic relapsing experimental allergic encephalomyelitis by transforming growth factor-beta 1. *J Immunol* 146: 3012–7.

81. Racke, M. K., A. Bonomo, D. E. Scott, B. Cannella, A. Levine, C. S. Raine, E. M. Shevach, and M. Rocken. 1994. Cytokine-induced immune deviation as a therapy for inflammatory autoimmune disease. *J Exp Med* 180:1961–6.

82. Segal, B. M., B. K. Dwyer, and E. M. Shevach. 1998. An interleukin (IL)-10/IL-12 immunoregulatory circuit controls susceptibility to autoimmune disease. *J Exp Med* 187:537–46.

83. Steinman, L. 1995. Escape from "horror autotoxicus": pathogenesis and treatment of autoimmune disease. *Cell* 80:7–10.

84. Matzinger, P. 1994. Tolerance, danger, and the extended family. *Annu Rev Immunol* 12:991–1045.

85. Janeway, C. A., Jr. 1992. The immune system evolved to discriminate infectious nonself from noninfectious self. *Immunol Today* 13:11–6.

86. Cyster, J. G., S. B. Hartley, and C. C. Goodnow. 1994. Competition for follicular niches excludes self-reactive cells from the recirculating B-cell repertoire [see comments]. *Nature* 371:389–95.

---

What is claimed is:

1. A method for inducing protective immunity against multiple sclerosis, the method comprising intramuscularly administering to a subject a naked DNA nucleic acid construct encoding a cytokine selected from the group consisting of macrophage inflammatory protein-1α (MIP-1α), monocyte chemoattractant protein 1 (MCP-1) and tumor necrosis factor-α (TNFα), operably linked to a viral transcription control sequence, to thereby induce protective immunity against multiple sclerosis.

2. The method of claim 1, wherein said transcription control sequence is selected from the group consisting of RSV control sequence, CMV control sequence, retroviral LTR sequence and SV-40 control sequence.

3. The method of claim 1, wherein said naked DNA nucleic acid construct is selected from the group consisting of pcDNA3, pcDNA3.1(+/−), pZeoSV2(+/−), pSecTag2, pDisplay, pEF/myc/cyto, pCMV/myc/cyto, pCR3.1, pCI, pBK-RSV, pBK-CMV, pTRES and their derivatives.

4. The method of claim 1, wherein said subject is a human.

* * * * *

SEQUENCE LISTING (1) GENERAL INFORMATION:

(iii) NUMBER OF SEQUENCES:    13

(2) INFORMATION FOR SEQ ID NO:1:

(i) SEQUENCE CHARACTERISTICS:
        (A) LENGTH:17
        (B) TYPE:amino acid
        (C) STRANDEDNESS:single
        (D) TOPOLOGY:linear (xi) SEQUENCE DESCRIPTION: SEQ ID NO:1:

Tyr Gly Ser Leu Pro Gln Lys Ser Gln Arg Ser Gln Asp Glu Asn
                5                    10                 15

Pro Val
    17

(2) INFORMATION FOR SEQ ID NO:2:

(i) SEQUENCE CHARACTERISTICS:
        (A) LENGTH:26
        (B) TYPE:nucleic acid
        (C) STRANDEDNESS:single
        (D) TOPOLOGY:linear (xi) SEQUENCE DESCRIPTION: SEQ ID NO:2:

ATGAAGGTCT CCACCACTGC CCTTGC                                26

(2) INFORMATION FOR SEQ ID NO:3:

(i) SEQUENCE CHARACTERISTICS:
        (A) LENGTH:25
        (B) TYPE:nucleic acid
        (C) STRANDEDNESS:single
        (D) TOPOLOGY:linear (xi) SEQUENCE DESCRIPTION: SEQ ID NO:3:

TCAGGCATTC AGTTCCAGCT CAGTG                                  25

(2) INFORMATION FOR SEQ ID NO:4:

(i) SEQUENCE CHARACTERISTICS:
        (A) LENGTH:24
        (B) TYPE:nucleic acid
        (C) STRANDEDNESS:single
        (D) TOPOLOGY:linear (xi) SEQUENCE DESCRIPTION: SEQ ID NO:4:

ATGAAGCTCT GCGTGTCTGC CTTC                                    24

(2) INFORMATION FOR SEQ ID NO:5:

(i) SEQUENCE CHARACTERISTICS:
        (A) LENGTH:24
        (B) TYPE:nucleic acid
        (C) STRANDEDNESS:single
        (D) TOPOLOGY:linear (xi) SEQUENCE DESCRIPTION: SEQ ID NO:5:

TCAGTTCAAC TCCAAGTCAT TCAC                                    24

(2) INFORMATION FOR SEQ ID NO:6:

(i) SEQUENCE CHARACTERISTICS:
        (A) LENGTH:24
        (B) TYPE:nucleic acid
        (C) STRANDEDNESS:single
        (D) TOPOLOGY:linear (xi) SEQUENCE DESCRIPTION: SEQ ID NO:6:

ATGAAGATCT CTGCAGCTGC ATCC                                    24

(2) INFORMATION FOR SEQ ID NO:7:

(i) SEQUENCE CHARACTERISTICS:
        (A) LENGTH:22
        (B) TYPE:nucleic acid
        (C) STRANDEDNESS:single
        (D) TOPOLOGY:linear (xi) SEQUENCE DESCRIPTION: SEQ ID NO:7:

CTAGCTCATC TCCAAATAGT TG                                      22

(2) INFORMATION FOR SEQ ID NO:8:

(i) SEQUENCE CHARACTERISTICS:
        (A) LENGTH:27
        (B) TYPE:nucleic acid
        (C) STRANDEDNESS:single
        (D) TOPOLOGY:linear (xi) SEQUENCE DESCRIPTION: SEQ ID NO:8:

ATGCAGGTCT CTGTCACGCT TCTGGGC                                27

(2) INFORMATION FOR SEQ ID NO:9:

(i) SEQUENCE CHARACTERISTICS:
        (A) LENGTH:24
        (B) TYPE:nucleic acid
        (C) STRANDEDNESS:single
        (D) TOPOLOGY:linear (xi) SEQUENCE DESCRIPTION: SEQ ID NO:9:

CTAGTTCTCT GTCATACTGG TCAC                                    24

(2) INFORMATION FOR SEQ ID NO:10:

(i) SEQUENCE CHARACTERISTICS:
        (A) LENGTH:20
        (B) TYPE:nucleic acid
        (C) STRANDEDNESS:single
        (D) TOPOLOGY:linear (xi) SEQUENCE DESCRIPTION: SEQ ID NO:10:

ATGAGCACAG AAAGCATGAT    20

(2) INFORMATION FOR SEQ ID NO:11:

(i) SEQUENCE CHARACTERISTICS:
        (A) LENGTH:21
        (B) TYPE:nucleic acid
        (C) STRANDEDNESS:single
        (D) TOPOLOGY:linear (xi) SEQUENCE DESCRIPTION: SEQ ID NO:11:

TCACAGAGCA ATGACTCCAA A    21

(2) INFORMATION FOR SEQ ID NO:12:

(i) SEQUENCE CHARACTERISTICS:
        (A) LENGTH:21
        (B) TYPE:nucleic acid
        (C) STRANDEDNESS:single
        (D) TOPOLOGY:linear (xi) SEQUENCE DESCRIPTION: SEQ ID NO:12:

CATCGTGGGC CGCTCTAGGC A    21

(2) INFORMATION FOR SEQ ID NO:13:

(i) SEQUENCE CHARACTERISTICS:
        (A) LENGTH:21
        (B) TYPE:nucleic acid
        (C) STRANDEDNESS:single
        (D) TOPOLOGY:linear (xi) SEQUENCE DESCRIPTION: SEQ ID NO:13:

CCGGCCAGCC AAGTCCAGAC G    21